United States Patent
Bikram

(10) Patent No.: US 8,975,079 B2
(45) Date of Patent: Mar. 10, 2015

(54) REDUCIBLE POLYMERS FOR NONVIRAL GENE DELIVERY

(75) Inventor: Malavosklish Bikram, Spring, TX (US)

(73) Assignee: University of Houston System, Houston, TX (US)

( * ) Notice: Subject to any disclaimer, the term of this patent is extended or adjusted under 35 U.S.C. 154(b) by 463 days.

(21) Appl. No.: 12/658,514

(22) Filed: Feb. 11, 2010

(65) Prior Publication Data

US 2010/0204301 A1 Aug. 12, 2010

Related U.S. Application Data

(60) Provisional application No. 61/207,392, filed on Feb. 11, 2009.

(51) Int. Cl.
*A61K 48/00* (2006.01)
*C12N 15/87* (2006.01)
*C08G 69/42* (2006.01)

(52) U.S. Cl.
CPC .............. *C12N 15/87* (2013.01); *C08G 69/42* (2013.01); *A61K 48/00* (2013.01)
USPC ........... 435/458; 435/325; 435/375; 435/455; 424/489; 514/44 A; 514/44 R; 530/322; 530/323

(58) Field of Classification Search
CPC . C08L 89/00; A61L 27/3604; A61L 27/3804; A61L 27/50; A61L 27/38; C08J 2389/00
USPC .......... 514/44, 1.1, 773; 424/94.1, 93.6, 93.7, 424/130.1; 435/395
See application file for complete search history.

(56) References Cited

U.S. PATENT DOCUMENTS

2006/0246585 A1* 11/2006 Nagasaki et al. ............. 435/455

FOREIGN PATENT DOCUMENTS

WO 2009061456 A2 5/2009
WO WO 2009062084 A2 * 5/2009

OTHER PUBLICATIONS

Christensen et al. Bioconjugate Chemistry, 17 (5). pp. 1233-1240.*
Christensen et al. Bioconjugate Chemistry, 17 (5). pp. 1233-1240. (2006).*
Bikram, M. et al. Biodegradable Poly(Ethylene Glycol)-co-poly(L-lysine)-g-histidine Multiblock Copolymers for Nonviral Gene Delivery: *Macromolecules*, 2004, vol. 37, pp. 1903-1916.
Ahn C. H. et al. Synthesis of Biodegradable Multi-Block Copolymers of Poly(L-lysine) and Poly(Ethylene Glycol) as a Non-Viral Gene Carrier: *Journal of Controlled Release*, 2004, vol. 97, pp. 567-574.
Parker, et al. "(LYS) 16-based reducible polycations provide stable polyplexes with anionic fusogenic peptides and efficient gene delivery to post mitotic cells", Biochimica Et Biophysica Acta (BBA)—General Subjects, Elsevier, vol. 1770, No. 9, Aug. 16, 2007, pp. 1331-1337, XP022201959, ISSN: 0304-4165, DOI: 10.1016/J BBAGEN. Jun. 6, 2007.
Read, ML, et al. "A versatile reducible polycation-based system for efficient delivery of a broad range of nucleic acids", Nucleic Acids Research, Information Retrieval LTD, vol. 33, No. 9, May 1, 2005, pp. e86-1, XP002447464, ISSN: 0305-1048, DOI: 10.1093/NAR/GNI085 [retrieved on May 24, 2005].
Read ML, et al. "Vector based on reducible polycations facilitate intracellular release of nucleic acids", Journal of Gene Medicine, John Wiley & Sons, Inc, US, vol. 5, No. 3, Mar. 1, 2003, pp. 232-245, XP002481542, ISSN: 1099-498X, DOI: 10.1002/JGM.331.

* cited by examiner

*Primary Examiner* — Janet Epps-Smith
(74) *Attorney, Agent, or Firm* — Benjamin Aaron Adler

(57) ABSTRACT

Provided herein are biodegradable copolymers and nanoplex delivery systems comprising the same and a cargo molecule, such as a nucleic acid, a polynucleotide or other biomolecule. The biodegradable copolymers may comprise a reducible polymer linearly modified with lysine, such as a linear lysine-modified N,N'-cystamine bisacrylamide. The biodegradable copolymers also may be conjugated to a sequestering moiety, such as dietheylamine. The biodegradable copolymers also may comprise one or both of a targeting moiety and one or more moieties to facilitate endosomal escape. Also provided are methods for treating a pathophysiological condition and for increasing biocompatibility of a polymeric delivery system upon delivery to a subject using the biodegradable copolymers and nanoplexes.

19 Claims, 13 Drawing Sheets

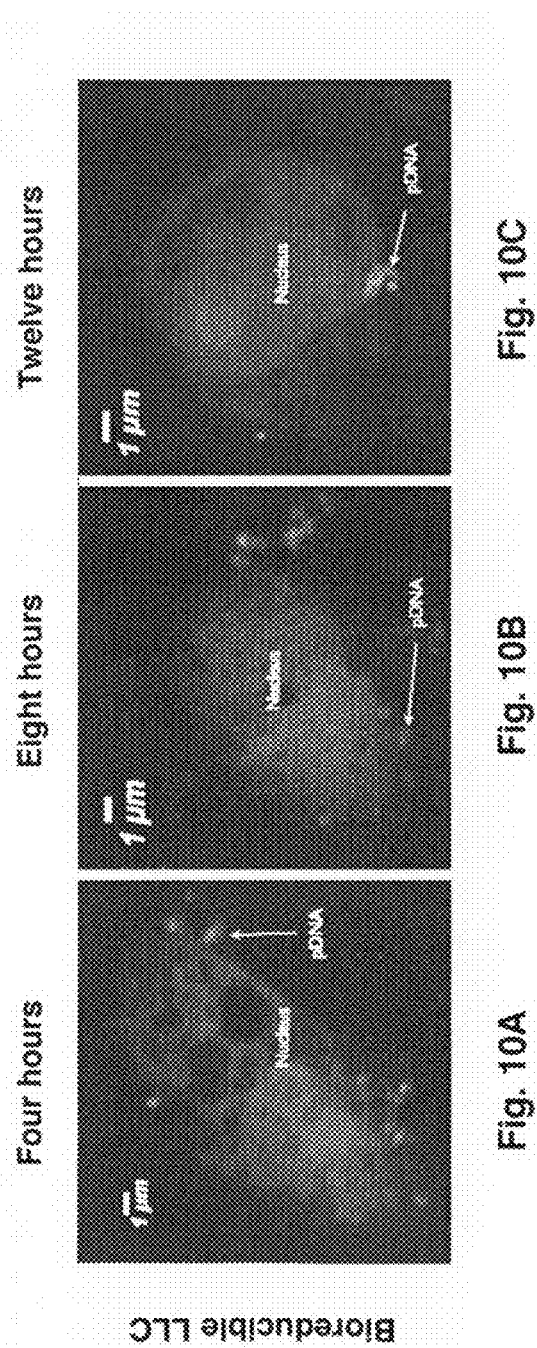

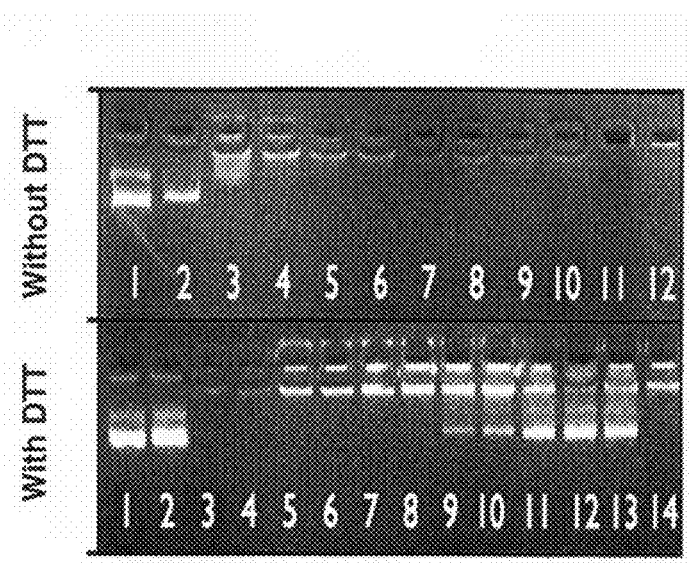
Fig. 11A
Fig. 11B
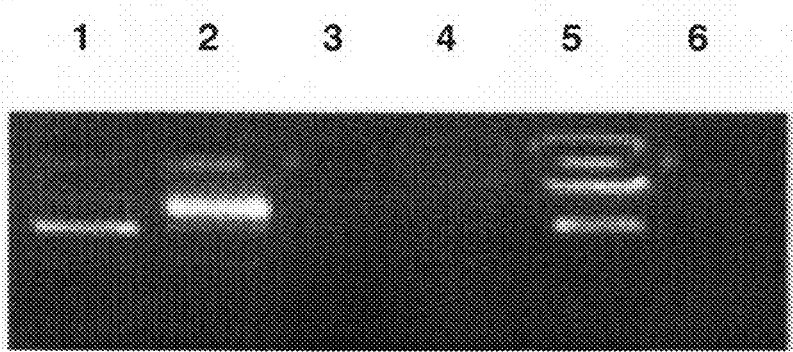
Fig. 12A

REDUCIBLE POLYMERS FOR NONVIRAL GENE DELIVERY

CROSS-REFERENCE TO RELATED APPLICATIONS

This nonprovisional application claims benefit of priority under 35 U.S.C. §119(e) of provisional application U.S. Ser. No. 61/207,392, filed Feb. 11, 2009, the entirety of which is hereby incorporated by reference.

BACKGROUND OF THE INVENTION

1. Field of the Invention

The present invention relates generally to the fields of copolymer chemistry and gene delivery systems. More specifically, the present invention relates to the design and synthesis of a novel biodegradable polymer, for example, reducible linear L-lysine-modified copolymers (LLC).

2. Description of the Related Art

During the last decade, there has been a rapid development of nonviral gene delivery systems based on cationic polymers for the treatment of both inherited and acquired diseases. This is due to the dissemination of many disease pathways in which the modulation of expressed proteins or genes via gene therapy has the potential of significantly improving the treatment options of patients. Natural cationic polymers such as chitosan (1) and atelocollagen (2) or synthetic cationic polymers including poly(L-lysine) (PLL) (3), poly(ethylenimine) (PEI) (4-6), and dendrimers (4,7) have been widely explored as a means of delivering therapeutic nucleic acids to target cells. However, even though cationic polymers have produced modest gene expression, their translation into a clinical setting has been severely mired by carrier-mediated cytotoxicities associated with their high charge densities and high molecular weights. Thus, biodegradable carriers have been designed to overcome these hurdles as well as to increase transfection efficiencies by facilitating the unpacking of the polymer/pDNA polyplexes after cellular uptake (8).

Previously, biodegradable polymers such as polyurethanes (PUs) that contain tertiary amines on the backbone and primary, secondary, and tertiary amines on the side chains have been synthesized as nonviral gene delivery vectors (9). To improve the solubility and biocompatibility of the polymers, glycidol was conjugated into the structure. These backbone modifications resulted in higher transfection efficiencies comparable to the well-known non-degradable gene carrier poly(2-(dimethylamino)ethyl methacrylate (PDMAEMA) and lower cytotoxicities. Similarly, hydrolytically degradable poly(_-amino esters) were developed as cationic polymers for gene transfer, which produced about four times higher gene expression in human embryonic stem cells with minimal toxicity (10). In addition, many other hydrolysable polymers such as poly(ester amines) (11-13), poly(esters) (14), ketalized PEI (15-17), chitosans (18), dendrimers (4,7), and polyphosphazenes (19-21) have been developed as alternatives to non-degradable polymers for gene delivery.

Recently, reducible disulfide-containing cationic polymers also have been extensively explored as alternatives to non-degradable gene delivery systems due to the difference in redox potential between the reducing cytoplasm and the oxidizing extracellular space (22). Thus, the inclusion of disulfide bonds within the polymeric carriers would render the polymers biodegradable as a result of the reduction of the bonds to free thiols in the cytosol followed by the concomitant release of the nucleic acid cargo. It was demonstrated that triggered release of pDNA following reduction of disulfide-containing poly(amido ethylenimines) (SS-PAEIs) within the cytosol of several cell lines increases transfection efficiency 20-fold compared with PEI (23).

Similarly, other studies have focused on developing reducible forms of PEI including disulfide cross-linked low molecular weight PEI (24-25), poly(amido ethylenediamine) polymer with multiple disulfide bonds (SS-PAEDs) (26-27), reducible poly(amido amine) (poly(DAH/CBA)) (8,28) and bioreducible cationic arginine-conjugated poly(cystaminebisacrylamide-diaminohexane) (poly(CBA-DAH-R)) (29). However, apart from PEI, there have been limited studies focused on developing other forms of reducible cationic polymers, which could potentially produce additional significant improvements over current nonviral delivery systems. Poly(L-lysine) and its derivatives have been shown to be very effective gene delivery carriers with much less cytotoxicity compared with PEI (30-36). However, these carriers also pose a significant problem of prolonged cytotoxicity in clinical applications due to their high molecular weight.

Thus, there is a recognized need in the art for improved biodegradable, biocompatible and reducible copolymers for useful in a biommolecule delivery system. More specifically, the prior art is deficient in disulfide-reducible linear L-lysine-modified copolymers. The present invention fulfills this long-standing need and desire in the art.

SUMMARY OF THE INVENTION

The present invention is directed to a biodegradable copolymer or a pharmaceutical composition thereof. The copolymer comprises a reducible polymer linearly modified with lysine. The present invention is directed to a related biodegradable copolymer further comprising a moiety effective to sequester a reactive group conjugated along the copolymer backbone. The present invention is directed to another related biodegradable copolymer further comprising a targeting moiety. The present invention is directed to yet another related biodegradable copolymer further comprising a targeting moiety one or more moieties effective to facilitate endosomal escape.

The present invention is directed to a related biodegradable, linear lysine-modified copolymer having the chemical structure:

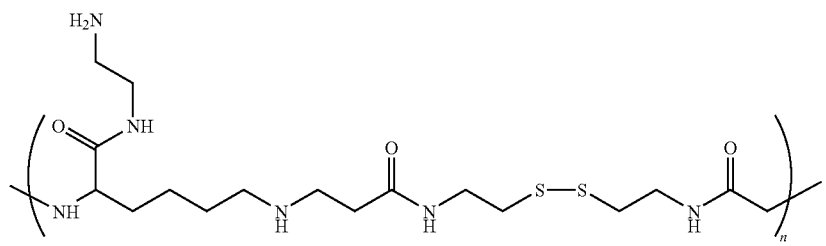

where n is 1 to about 10 repeating units.

The present invention also is directed to a nanoplex delivery system. The delivery system comprises the biodegradable copolymer described herein; and a cargo molecule complexed thereto.

The present invention is directed to a related nanoplex delivery system comprising the biodegradable, linear lysine-modified copolymer having the chemical structure described supra and a nucleic acid or polynucleotide complexed thereto.

The present invention is directed further to a method for treating a pathophysiological condition in a subject. The method comprises delivering the cargo molecule comprising the nanoplex delivery system described herein one or more times to a cell associated with the pathophysiological condition in the subject, where transfection of the cell with the cargo molecule elicits a therapeutic response, thereby treating the pathophysiological condition. The present invention is directed to a related method further comprising administering one or more times concurrently or consecutively one or more other therapeutic compounds or pharmaceutical compounds to the subject.

The present invention is directed further still to a method for increasing biocompatibility of a polymeric delivery system upon delivery to a subject. The method comprises synthesizing a linear copolymer from a polymer comprising a reducible bond along the polymer backbone and lysine and complexing the synthesized linear lysine-modified copolymer with a biomolecule thereby forming a nanoplex. The nanoplex is delivered to the subject whereupon reduction of the polymer backbone, the biomolecule is released from the nanoplex and the nanoplex degrades into biodegradable lysine subunits, thereby improving biocompatibility of the polymeric delivery system with the subject. The present invention is directed to a related method further comprising conjugating diethylamine along the copolymer backbone to sequester lysine hydroxyl groups. The present invention is directed to another related method further comprising conjugating one or both of a targeting moiety or one or more moieties effective to facilitate endosomal escape to the linear lysine-modified copolymer.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 8D shows the transfection efficiency of reducible LLCs, Lipofectamine® and branched PEI as a percentage of EGFP positive cells per total amount of HDF cells. Data represented as mean±SD, N=3 (*, ‡ indicate p-value>0.05).

FIGS. 10A-10C show confocal microscopy images of transfected HDF cells with EMA-labeled pCMV-Luc using reducible LLCs at N/P ratio of 25/1 after four (FIG. 10A), eight (FIG. 10B) and twelve hours (FIG. 10C) post transfection.

FIGS. 11A-11B show the agarose gel electrophoresis of final LLC polymer with plasmid DNA polyplexes at different nitrogen/phosphate (N/P) ratios at the conditions of without DTT (Lane 1, naked pDNA; lanes 2-11, LLC/pDNA at N/P ratios of 1:1, 5:1, 10:1, 15:1, 20:1, 25:1, 30:1, 40:1. 50:1 and 100:1 and lane 12, PLL/pDNA at N/P ratio of 25:1) (FIG. 11A) and with increasing concentrations of DTT incubation at 37° C. for 30 minutes (Lane 1, naked pDNA; lanes 2-12, LLC/pDNA at N/P ratio of 25:1 with increasing concentrations of DTT (0.1, 0.25, 0.5, 0.75, 1, 1.5, 2, 2.5, 3, 3.5 and 4 nM of DTT) and lane 13, PLL/pDNA at N/P ratio of 25:1 with 4 nM DTT) (FIG. 11B).

FIGS. 12A-12B shows the effect of DTT on the release of EMA-labeled pCMV-Luc from LLC/pDNA polyplexes using fluorescence spectroscopy and gel electrophoresis. Lanes 1-6 in FIG. 12A represented free DNA, DNA with 4 mM of DTT, LLCs with DNA, PLL with DNA, LLCs with DNA and 4 mM of DTT and PLL with DNA and 4 mM DTT respectively.

DETAILED DESCRIPTION OF THE INVENTION

Figure 1:
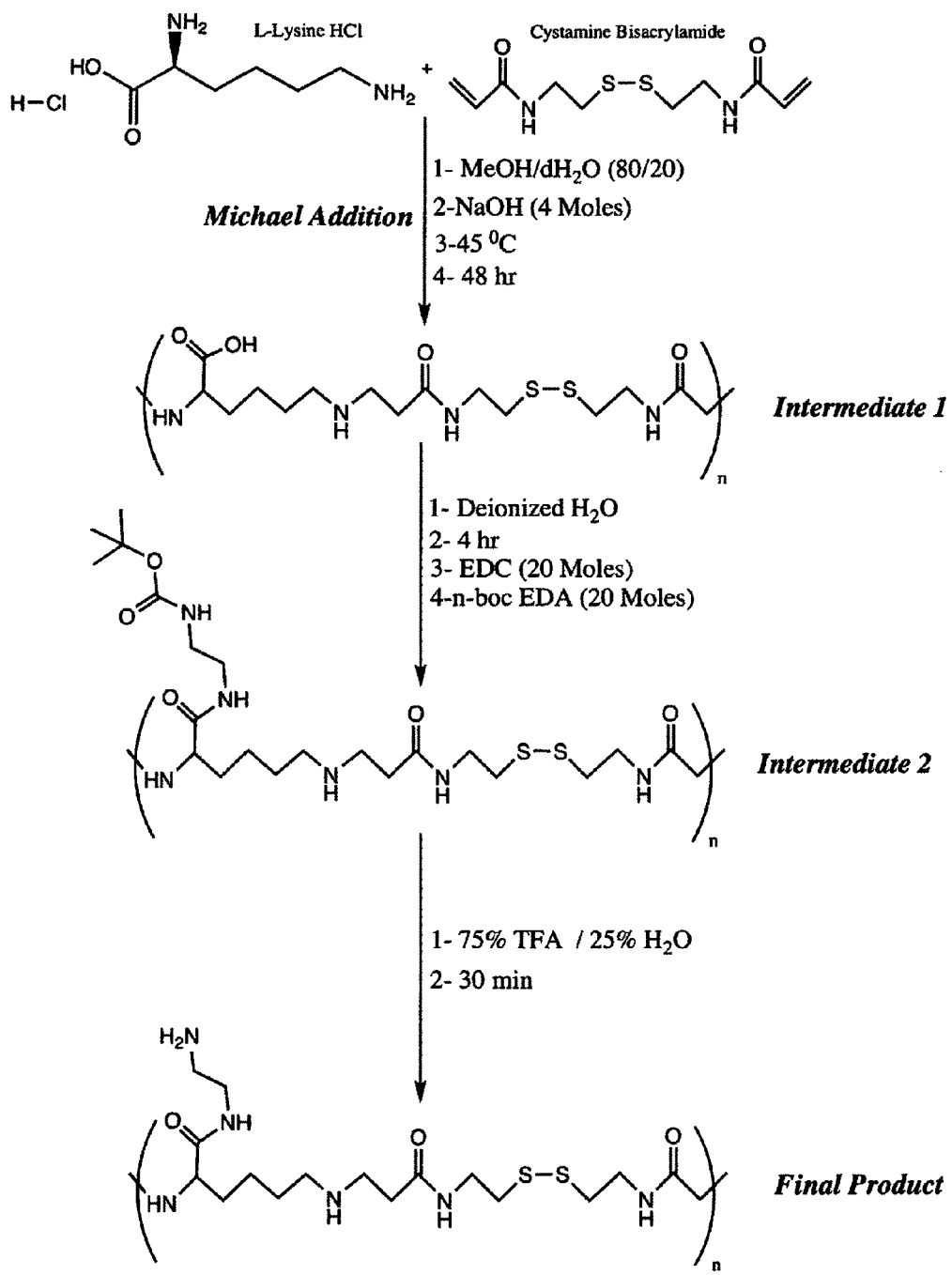
FIG. 1 is the synthetic scheme for the biodegradable linear lysine copolymers (LLC).

As used herein, the term "a" or "an", when used in conjunction with the term "comprising" in the claims and/or the specification, may refer to "one," but it also is consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

As used herein, the term "or" in the claims is used to mean "and/or" unless explicitly indicated to refer to alternatives only or the alternatives are mutually exclusive, although the disclosure supports a definition that refers to only alternatives and "and/or."

As used herein, the term "linear copolymer" refers to a polymer derived from two (or more) monomeric species comprising a single main chain. The linear lysine-modified copolymers described herein may comprise, but are not limited to, a plurality of units with lysine-modified N,N'cystamine bisacrylamide (CBA). The linear copolymer may be further modified along the copolymer backbone with moieties suitable to enhance complexation with a nucleic acid, such as DNA, plasmid DNA (pDNA) or a gene and/or with targeting moieties or moieties effective to facilitate endosomal escape.

As used herein, the term "N/P ratio" refers to the number of nitrogen residues of the copolymer per DNA phosphates in the complex.

As used herein, the term "subject" refers to any recipient of the reducible linear lysine-modified copolymers and/or the nanoplexes comprising the same.

In one embodiment of the present invention there is provided a biodegradable copolymer, comprising a reducible polymer linearly modified with lysine. Further to this embodiment the biodegradable copolymer may comprise a moiety effective to sequester a reactive group conjugated along the copolymer backbone. In this further embodiment the reactive group is the lysine hydroxyl group and the sequestering moiety is diethylamine. In another further embodiment the biodegradable copolymer may comprise a targeting moiety. In another further embodiment the biodegradable copolymer may comprise one or more moieties effective to facilitate endosomal escape.

In all embodiments the reducible polymer may comprise a disulfide bond. The reducible polymer may be N,N'cystamine bisacrylamide.

In an aspect of these embodiments the biodegradable copolymer may comprise a linear lysine modified N,N'cystamine bisacrylamide and a diethyleneamine conjugated to the lysine hydroxy group. The biodegradable copolymer may have the following chemical structure where n is 1 to about 10 repeating units. Preferably, n is about 6 to about 8 repeating units

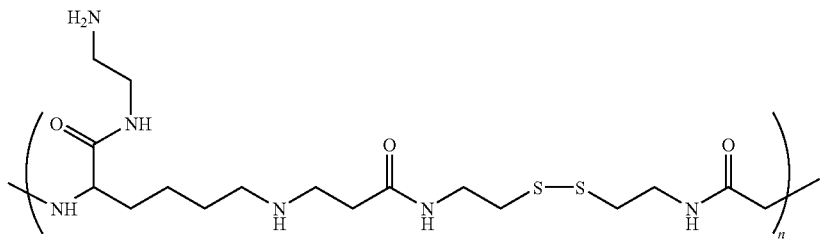

In a related embodiment the present invention provides a biodegradable, linear lysine-modified copolymer having the chemical structure described supra where n is 1 to about 10 repeating units.

In another related embodiment all the biodegradable copolymers, as described supra, may comprise a pharmaceutical composition and a pharmaceutically acceptable carrier.

In another embodiment of the present invention there is provided a nanoplex delivery system, comprising the biodegradable copolymer, as described supra and a cargo molecule complexed thereto. In this embodiment the cargo molecule may comprise a nucleic acid, a polynucleotide or other biomolecule. Representative examples of the cargo molecule are DNA, plasmid DNA, siRNA, introgens, or antisense nucleotides. Also, the nanoplex may have a nitrogen:phosphate ratio of about 1:1 to about 50:1.

In a related embodiment of the present invention there is provided a nanoplex delivery system, comprising the biodegradable, linear lysine-modified copolymer having the chemical structure as described supra and a nucleic acid or polynucleotide complexed thereto.

In yet another embodiment of the present invention there is provided a method for treating a pathophysiological condition in an subject, comprising delivering the cargo molecule comprising the nanoplex delivery system, as described supra, one or more times to a cell associated with the pathophysiological condition in the subject, where transfection of the cell with the cargo molecule elicits a therapeutic response, thereby treating the pathophysiological condition. Further to this embodiment the method comprises administering one or more times concurrently or consecutively one or more other therapeutic compounds or pharmaceutical compounds to the subject.

In yet another embodiment of the present invention there is provided a method for increasing biocompatibility of a polymeric delivery system upon delivery to a subject, comprising synthesizing a linear copolymer from a polymer comprising a reducible bond along the polymer backbone and lysine; complexing the synthesized linear lysine-modified copolymer with a biomolecule thereby forming a nanoplex; and delivering the nanoplex to the subject, whereupon reduction of the polymer backbone, the biomolecule is released from the nanoplex and the nanoplex degrades into biodegradable lysine subunits, thereby improving biocompatibility of the polymeric delivery system with the subject.

Further to this embodiment the method comprises conjugating diethylamine along the copolymer backbone to sequester lysine hydroxyl groups. Further still the method comprises conjugating one or both of a targeting moiety or one or more moieties effective to facilitate endosomal escape to the linear lysine-modified copolymer.

In all embodiments the reducible bond is a disulfide bond. Also, the polymer may be N,N'cystamine bisacrylamide. In addition, the biomolecule may be a nucleic acid or a polynucleotide. Representative examples are a DNA, a plasmid DNA, an siRNA, an nitrogen, or an antisense nucleotide. In an aspect of these embodiments the linear lysine-modified copolymer may have the chemical structure and n repeating units as described supra.

Provided herein are novel biodegradable copolymers suitable for non-viral delivery of a nucleic acid. The copolymers may comprise a reducible linear L-lysine-modified copolymer (LLC) which comprises a reducible disulfide bond in the polymer backbone. A representative unit of the copolymer is shown in Example 1.

The LLCs of the present invention may be synthesized using standard and well-known chemical synthetic procedures. A Michael addition reaction is utilized to form a covalent bond between the lysine sidechain amino group and the beta alkenyl carbon of an acrylamide moiety of N,N'cystamine bisacrylamide (CBA) to form the linear copolymer. The copolymer backbone comprises disulfide bonds in main chains, which are totally stable in an extracellular oxidizing environment and are degraded rapidly in an intracellular reducing environment. The lysine-modified copolymer may comprise about 1-10 polymeric repeating units, preferably 6-8 repeating units.

The LLCs may be further conjugated to a moiety, such as, but not limited to, diethyleneamine, along the copolymer backbone suitable to increase or improve complexation with a nucleic acid or polynucleotide. In the linear lysine-modified copolymers presented herein, diethyleneamine is suitable to sequester the free lysine hydroxyl group. This backbone modification allows a cargo, such as plasmid DNA, other polynucleuotides, e.g., siRNA, introgens or antisense nucleotides, or other biomolecules to be complexed efficiently with the cationic copolymer to form stable and small particle sized nanoplexes that enhance transfection efficiencies.

The linear lysine-modified copolymers further may comprise a targeting moiety to facilitate delivery of the LLC complexed to a nucleic acid to a cell of interest. Effective targeting moieties are standard and well-known in the art and may include, inter alia, antibodies, receptor ligands and other peptides. Also, the LLCs further may comprise known and standard molecules and/or moieties suitable to facilitate endosomal escape, for example, but not limited to an ionophore.

Thus, the linear lysine-modified copolymers comprise a delivery vehicle and may form nanoplexes with a suitable nucleic acid or polynucleotide. The polyplexes may have an N/P ratio from about 1/1 to about 50/1. The polyplexes may be delivered to the cell cytosol using standard and well-known transfection techniques. It is contemplated that the LLCs are effective to deliver a nucleic acid to the cell nucleus.

Upon reduction of the polymer backbone, the DNA load is released into the cytoplasm allowing efficient gene or other nucleic acid or polynucleotide delivery. With respect to biodegradability, upon cleavage of the disulfide bond within the polymer backbone, the broken down subunits, which are lysine monomer units, are completely biodegradable. In addition, conjugation of the ethylenediamine component within the polymer backbone with an 80% conjugation efficiency enhances polymer water solubility and increases polymer backbone cationic charge which subsequently increases nucleic acid binding affinity. Thus, methods of improving delivery of a therapeutic or other molecule to a cell are provided and of increasing the biocompatibility of the LLCs and nanoplexes in a subject are provided.

As such, the biodegradable, reducible LLC:DNA nanoplexes may be used to treat a pathophysiological condition in a subject, for example, a cancer or other disease or disorder for which the DNA or polynucleotide complexed with the LLCs would provide a therapeutic benefit upon transfection and expression. It also is contemplated that the LLCs can form nanoplexes with other biomolecules effective to elicit a therapeutic effect upon delivery to one or more cells associated with the pathophysiological condition. As is known in the art the biodegradable LLCs or the nanoplexes may comprise a pharmaceutical composition having a pharmaceutically acceptable carrier. The nanoplexes may be administered one or more times to the subject. The nanoplexes or pharmaceutical compositions may be administered with one or more other therapeutic molecules or pharmaceuticals either concurrently or consecutively. It is well-known in the art to determine an effective dose and dosage schedule depending on the pathophysiological condition and its progression or remission and, inter alia, the age, sex, and health of the subject.

The following examples are given for the purpose of illustrating various embodiments of the invention and are not meant to limit the present invention in any fashion:

EXAMPLE 1

Materials and Methods

Chemicals and Equipment

N-butyloxycarbonyl ethylenediamine, L-lysine HCl, hyperbranched polyethylenimine (bPEI, Mw 25 kDa), trifluoroacetic acid (TFA), poly L-Lysine (PLL; MW 20.9 kDa), dithiothreitol (DTT), ethidium bromide (EtBr), cesium chloride (CsCl), ninhydrin reagent, and 3-(4,5-dimethyl-2-thiazolyl)-2,5-diphenyl-2H-tetrazolium bromide (MTT) are purchased from Sigma-Aldrich (St. Louis, Mo.). N,N-cystaminebisacrylamide (CBA) is purchased from PolySciences, Inc. (Warrington, Pa.). Dulbecco's Modified Eagle's Medium (DMEM), penicillin-streptomycin, fetal bovine serum (FBS), trypsin-like enzyme (TrypLE Express), Maxiprep kit, and Dulbecco's phosphate buffered saline (PBS) are purchased from Invitrogen-Gibco (Carlsbad, Calif.). Luciferase assay system with reporter lysis buffer and RQ1 RNase-free DNase I enzymes are purchased from Promega (Madison, Wis.). SlowFade® Gold antifade reagent, ethidium monoazide and DAPI are purchased from Invitrogen (Carlsbad, Calif.). PD-10 column is purchased from Pharmacia Biotech (Uppsala, Sweden). Bicinchoninic acid protein assay reagent (BCA) kit is purchased from Pierce (Rockford, Ill.). All materials and solvents are used as received without further purification.

Formazan concentration is determined with a BioTek instruments' ELx800™ system equipped with BioTek's Gen5™ Reader Control and Data Analysis Software (Winooski, Vt.). Chemluminescence generated from the luciferin protein is assayed using BioTek Instruments Synergy 2 luminometer system equipped with BioTek's Gen5™ Reader Control and Data Analysis Software (Winooski, Vt.). $^1$H NMR spectra are obtained using a General Electric (GE) QE-300 300 MHz, (Boston, Mass.) and chemical shifts (δ) are reported in parts per million (ppm). Matrix assisted laser desorption ionization time-of-flight (MALDI-TOF) data are obtained using a Voyager-DE STR Biospectrometry Workstation from Applied Biosystems (Foster City, Calif.). The molecular weights of the various polymers are determined by size exclusion chromatography (SEC) on a Shimatzu Prominence HPLC system (Shimadzu Scientific Instruments, MD) equipped with a Shodex SB-803-HQ (Particle size=6 nm) and Shodex SB-806-HQ (particle size=13 nm) columns in series and detected with photodiode array (PDA) and ELSD-LTII (Low temperature evaporative light scattering detector) detectors (Columbia, Md.). pH measurements are determined with a Corning pH meter 340 purchased from Corning Incorporated (Corning, N.Y.). Particle size and zeta potential (ζ) of the nanoplexes are determined with BI-200SM dynamic light scattering instrument (DLS, Brookhaven Instrument Corporation, Holtsville, N.Y.).

Fluorescence microscopy data is obtained using a fluorescence microscope (Olympus BX 51 Series) equipped with digital image capturing system connected to a UNIX based workstation (Spot® Diagnostic Instruments, D10 BXF) poared by Spot® software version 4.6.1.2 and Zeiss LSM 310 confocal microscope (Thornwood, N.Y.) with an Omnichrome external Ar/Kr ion laser (Melles Griot, Irvine, Calif.). Finally, confocal microscopy is performed using an Olympus Fluoview® 1000 confocal laser scanning microscope on an inverted IX 81 frame (Center Valley, Pa.). Images are collected using 358 (DAPI range), 541 (TRITC range) dichroic mirrors and spectral channels 1 and 2 on the confocal microscope. A 75 W xenon lamp is used to project broad-spectrum light through the pattern, which is focused with an Olympus 60× water immersion objective.

DNase I Protection Assay with LLC

To confirm the ability of the LLC to protect plasmid DNA from endonucleases, a DNase I protection assay is performed in vitro (24) LLC/pCMV-Luc complexes are prepared at a 25/1 N/P ratio with a final pDNA concentration of 0.01 mg/mL. 6 units (6U) RQ1 RNase-free DNase I is then added to either naked pCMV-Luc (12 µg) or complexes (12 µg pDNA) and the samples are incubated at 37° C. Then, 100 µL aliquots are removed at 0, 20, 40, 60, and 120 min postincubation and added to separate labeled tubes containing 100 µL of stop solution (200 mM NaCl, 20 mM EDTA, 1% SDS). The tubes are then incubated at 60° C. overnight to dissociate the pDNA from the complexes. The samples are electrophoresed and analyzed on a 1% agarose gel that is stained with ethidium bromide (0.5 µg/mL). Afterwards, DTT is added to all of the samples upto a concentration of 4 mM. The tubes are then incubated at 25° C. for 60 minutes. The samples are then electrophoresed and analyzed on a 1% agarose gel that is stained with ethidium bromide (0.5 µg/mL).

Particle Size and Zeta Potential (ζ) Measurement

Polyplexes are formed as described above and incubated for 30 minutes prior to measurements. The polyplexes are then diluted in 1 mL of 5% glucose and the average particle sizes and zeta potential of polyplexes are measured using a BI-200SM dynamic light scattering instrument (DLS, Brookhaven Instrument Corporation, Holtsville, N.Y.). Measurements are made at 25° C. using an ion-argon laser (λ=677 nm) as the instrument beam at a scattering angle of 90°. For data analysis, the viscosity (0.8905 mPa s) and refractive index (1.333) of pure water at 25° C. are used and measurements for particle size are reported as the effective mean diameters. Smoluchowski's equation is used to calculate the zeta potential values from the electrophoretic mobility. Measurements for each sample are repeated three times and reported as mean values±standard deviations.

Gel Retardation Assay

To evaluate the ability of the synthesized optimized reducible LLC copolymer synthesized with 20 molar excess of EDC and N-boc ethylenediamine to complex pDNA, a gel retardation assay is performed with a plasmid coding for the luciferase gene (pCMV-Luc). The polymer/pDNA complexes are prepared by mixing 1 µg of the pCMV-Luc plasmid with increasing amounts of synthesized reducible LLC in 5% glucose to form complexes at different N/P ratios. The polymer/pDNA complexes at predetermined N/P ratios of 1/1, 5/1, 10/1, 15/1, 20/1, 25/1, 30/1, 40/1 and 50/1 are then subjected to electrophoresis on a 1% (w/v) agarose gel containing 0.5 µg/mL ethidium bromide for 30 min at 120V in 1× tris-acetate-EDTA (TAE) buffer. The gel is run at 120V for 30 min and the location of the DNA bands is visualized with a UV transilluminator (254 nm) using Alpha Innotech FluoChem™ 8900 MultiImage™ Light cabinet operated through AlphaEaseFC™ gel documentation software.

DTT Reduction of LLC: Gel Retardation Assay Using DTT Reagent

To demonstrate the mechanism of pDNA release from polymer/pDNA complexes, a solution of optimized LLC/pDNA polyplexes at an N/P ratio of 25/1 are prepared as described above and the DTT reagent is added at different concentrations from 0.1 to 4 mM. For this study, an N/P ratio of 25/1 is used as it showed maximum DNA condensation. Polyplexes are incubated in Eppendorf tubes at room temperature for 30 min. After incubation, the polyplexes are electrophoresed on a 1% agarose gel containing ethidium bromide with tris-acetate-EDTA (TAE) running buffer at 120 V for 30 min. The location of the DNA bands is visualized with a UV illuminator (254 nm) using a gel documentation system.

DTT Reduction of LLC: Fluorescence Spectroscopy Using DTT Reagent

To determine whether all of the pDNA was released from the LLC/pDNA polyplexes, the reduction of the disulfide bonds with DTT was monitored with fluorescence microscopy. Briefly, LLCs were complexed with EMA-labeled pCMV-Luc for 60 min at an optimized N/P ratio of 25/1. Afterwards, 4 mM of DTT was added and the fluorescence was monitored for 120 min. The excitation and emission wavelengths were 480±20 nm and 600±35 nm respectively. All of the fluorescence spectroscopy data were normalized against the free pDNA and pDNA with 4 mM DTT fluorescence. Each sample was prepared in triplicates and the data was reported as mean±standard deviations.

In Vitro Transfection Efficiencies of LLC/pDNA Polyplexes

LLC mediated transfection is evaluated in HDFs, 4T1s, and MCF-7s cells by using the reporter plasmid pCMV-Luc. HDFs and MCF-7s are maintained in DMEM containing 10% FBS, streptomycin (100 µg/mL) and penicillin (100 units/mL) at 37° C. in a humidified atmosphere with 5% $CO_2$ and RPMI media is used for the 4T1 cell line. Cells are seeded in 6-well plates at a density of $5 \times 10^5$ cells/well for at least 24 hrs prior to transfection. DNA is complexed with the LLC and PLL at predetermined N/P (1, 5, 10, 15, 20, 25, 30, 40 and 50) ratios in phosphate buffer and incubated for 30 min before use. At the time of transfection, the medium in each well is replaced with fresh serum-free medium. Polyplexes (2 µg DNA/well) are incubated with the cells for 4 hrs at 37° C. The media is then replaced with 2 ml of fresh complete medium and the cells are incubated for an additional 44 hrs. The cells are then washed with PBS, treated with 200 µL cell lysis buffer, and incubated for 15 min. Cellular debris is removed by centrifugation at 8,000 rpm for 2-3 min.

The luciferase activity in the cell lysate (25 µL) is measured using a luciferase assay kit (100 µL luciferase assay buffer) on a BioTek Instruments Synergy 2 chemiluminometer. The relative luminescent unit (RLU) of luciferase expression is normalized against the protein concentration in the cell extracts as measured with a BCA protein assay kit. The LLC/pDNA polyplexes that produced the highest transfection efficiency with the least cytotoxicity in the cell lines tested was designated as the optimized N/P ratio and utilized in subsequent studies. Each sample was prepared in triplicates and the data was reported as mean±standard deviations.

LLC-mediated transfections were evaluated in HDFs cells as described in the previous section with the exception of using complete DMEM media containing 10% fetal bovine serum (FBS) instead of serum-free media. DNA was complexed with the LLCs or PLL control at the N/P ratio that gave the highest transfection efficiency in this cell line for both polymers based on the serum free transfection study (N/P ratio of 50/1 for PLL and N/P ratio of 40/1 for LLC in HDF cells). Each sample was prepared in triplicates and the data was reported as mean±standard deviations.

Fluorescence Microscopy of HDF Cells Transfected with Commercial Vectors

In order to evaluate the transfection efficiency of LLCs compared to other standard commercial nonviral gene delivery vectors, HDF cells were transfected with bPEI and Lipofectamine® complexed with the pCMV-EGFP plasmids at an optimized N/P ratio of 25/1 (least cytotoxicity as described above) and 10/1 for LLCs and bPEI respectively. The optimized N/P of 10/1 for bPEI was chosen as it yielded the highest transfection efficiency with the least cytotoxicity in HDF cells (data not shown). In addition, Lipofectamine®/pDNA conjugates were prepared as per the manufacturer's instructions. Briefly, HDF cells were cultured on 2×2 glass slides placed into the wells of a 6 well plate. Following a PBS wash, polyplexes prepared with pCMV-EGFP were added to the cells, which were incubated for an additional 4 hr. The cells were washed in 1×PBS, pH 7.4 and fixed in 2% freshly prepared formaldehyde for 15 min. The HDF cells expressing EGFP were imaged and counted using an Olympus BX 51 Series fluorescence microscope per total amount of cells. The maximum excitation and emission wavelengths for EGFP detection were 488±20 nm and 509±20 nm respectively.

MTT Cytotoxicity Assay

HDF, MCF-7s, and 4T1s cells are seeded in a 6-well plate at a density of $5.0 \times 10^5$ cells/well and incubated for at least 24 hrs. pCMV-Luc is complexed with the LLC and PLL at predetermined N/P ratios (1, 5, 10, 15, 20, 25, 30, 40 and 50) in 5% glucose and incubated for 30 min. Polyplexes (2 µg DNA/well) are incubated with the cells for 4 hrs in serum-free media followed by 20 hrs in complete media. MTT solution (120 µL, 2 mg/mL in PBS) is then added to the cells, which are incubated for an additional 4 hrs at 37° C. Afterwards, the media is removed and 750 µL DMSO is then added to each well. The absorption is measured at 570 nm using a BioTek Instrument ELx800™ microplate reader. The percentage cell viability of each sample is determined relative to the control (untreated) cells as shown in equation 1. In equation 1 the percentage cell viability is calculated based on the absorbance of transfected and untransfected cells. All cytotoxicity experiments are performed in triplicates. Each sample is prepared in triplicates.

Eq. (1)

$$\text{Cell Viability (\%)} = \frac{\text{Sample } OD_{570}}{\text{Control } OD_{570}} \times 100 \quad (1)$$

where:
Sample $OD_{570}$: Absorbance of the transfected cells.
Control $OD_{570}$: Absorbance of the untransfected cells.

Confocal Microscopy Study of HDF Cells Transfected with EMA Labeled pDNA

To determine whether or not pDNA released from LLC/pDNA polyplexes as a result of the reduction of the disulfide bonds of the LLCs would be observed in the cytosol of treated cells, we viewed cells treated with LLC/EMA-labeled pDNA polyplexes with confocal microscopy. Briefly, HDFs were cultured on 2×2 glass slides placed into the wells of a 6-well plate. The cells were then washed with 1×PBS buffer and transfected with polyplexes prepared with EMA-labeled pCMV-Luc for 4 hr as described previously. The cells were washed and fixed with 2% freshly prepared formaldehyde in 1×PBS buffer for 15 min at predetermined time intervals of 0, 4, 8, and 12 hr. The cells were then counterstained with a 10 µg/ml 4,6-diamidino-2-phenylindole (DAPI) solution to visualize the cells' nuclei. The labeled cells were then imaged using an Olympus BX 51 confocal laser scanning microscope on an inverted IX 81 frame. The EMA-labeled pDNA was excited using 488-541 nm illumination (TRITC range), while the DAPI stain was imaged at 358 nm.

Cell Lines

Human dermal fibroblasts (HDFs), human breast adenocarcinoma cells (MCF-7s) and metastatic mouse breast cancer cells (4T1 s) are purchased from American Type Culture Collection (ATCC) (Manassas, Va.) and is cultured in DMEM medium (HDFs and MCF-7s) and RPMI medium (4T1s) supplemented with 10% FBS and maintained at 37° C. in a humidified atmosphere of 5% $CO_2$. Mouse adipose stromal cells (MA) were a generous gift from Professor Ke-He Ruan (University of Houston) and cultured in DMEM-F12 medium supplemented with 10% Newborn Calf Serum (NCF) and maintained as above.

Amplification and Purification of pCMV-EGFP and pCMV-Luc

A firefly luciferase reporter gene is inserted into a pCI plasmid vector driven by the (CMV) cytomegalovirus immediate-early promoter (Promega, Madison, Wis.) to yield the pCMV-Luc plasmid, which is amplified in E. coli DH5α and isolated by standard Maxiprep kit. The pCMV-Luc and pCMV-EGFP (enhanced green fluorescent protein construct under the control of the CMV promoter) vectors are a generous gift from Professor Sung Wan Kim (University of Utah). The plasmids are amplified via transformation into DH5α competent cells and purified using a QIAGEN Endofree Maxi Plasmid Purification kit.

Labeling of pCMV-Luc with Ethidium Monoazide pCMV-Luc pDNA is fluorescently labeled with the fluorophore ethidium monoazide (EMA). To 200 µg of pCMV-Luc in 2 ml of $H_2O$ is added 5 µg of ethidium monoazide. The solution is exposed to UV light of principal wavelength 312 nm for 2 min after incubation for 10 minutes. PD-10 columns are then used to purify the plasmid. CsCl is added to a concentration of 1.1 g/ml to remove intercalated but not covalently bound ethidium and is gently mixed until it dissolved. Sodium citrate saturated isopropanol is then added and the upper phase, which contained the unbound ethidium is discarded. The isopropanol ishing is repeated until the upper phase appeared clear. The DNA in the bottom layer is then precipitated overnight at −20° C. with 8 volumes of a 1:3 TE/absolute ethanol solution.

Statistical Analysis

The data are presented as means of at least three replicates and standard deviations; differences are analyzed using the two-tailed student's t-test and a probability of less than or equal 0.001 is taken as very highly significant (*), between 0.01 and 0.001 is considered highly significant () and between 0.05 and 0.01 is taken as significant (*). GraphPad Prism® version 5 is used to conduct the statistical analysis.

EXAMPLE 2

Polymer Synthesis

Synthesis of Reducible Linear L-Lysine-Modified Copolymers (LLC) Without Ethylenediamine

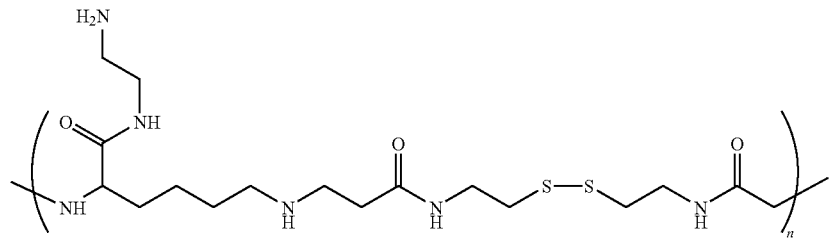

The lysine monomers are activated by neutralization of the acid form of the amino acid with sodium hydroxide (NaOH). The activated lysine is then reacted with CBA in a Michael addition reaction. Briefly, 730.6 mg (4 moles) L-lysine HCl and 1060 mg (4 moles) CBA are weighed and transferred to a 50 mL round bottom flask. Afterwards, 160 mg (4 moles) of NaOH is used to neutralize the HCl present in the L-lysine starting material. Then, 10 mL of methanol/water (MeOH/$H_2O$) mixture of 80/20 volume ratio are added to the flask, which is then stirred in an oil bath at 45° C. to dissolve the reagents. The reaction is then stirred in the dark under a nitrogen atmosphere for 2 days (FIG. 1, Intermediate 1). The resulting solution is then dissolved in ultrapure water and the reaction solution is purified via dialysis (MWCO 2000) against water for 2 days to remove low molecular weight polymeric biproducts and remaining traces of the starting materials. The dialyzed solution is then transferred to a sterile conical tube and lyophilized for 2 days.

The resulting polymers are characterized with proton nuclear magnetic resonance ($^1$H NMR), gel permeation chromatography (GPC), and matrix assisted laser desorption ionization-time of flight (MALDI-TOF). The molecular weights of the various polymers are determined with size exclusion chromatography (SEC) and mass spectrometry with MALDI ionization. The mobile phase for SEC interfaced with an evaporative light scattering detector (ELSD) maintained at 40° C. is ammonium acetate buffer (0.15 M) of pH 4.4 with methanol (80/20) pumped at a rate of 1 mL/min. A polyethylene glycol standard kit is used to construct the calibration curves. The matrix for MALDI-TOF is saturated alpha-cyano-4-hydroxycinnamic acid dissolved in 50/50 acetonitrile/water with 0.1% TFA with a polymer concentration of 1 mg/ml. An equal volume (8 μL) of the polymer and the matrix prepared are spotted and air-dried on the plate.

Conjugation of N-boc Ethylenediamine to Synthesized Reducible LLC

To sequester the free hydroxyl groups in intermediate 1, which can reduce complexation with pDNA, N-boc ethylenediamine is selectively conjugated along the polymer backbone. In addition, to optimize the conjugation of N-boc ethylenediamine, 5 different copolymers are prepared by varying the amounts of EDC and N-boc. Briefly, 100 mg each of reducible LLC (0.033 mmoles) are weighed and transferred to five different round bottom flasks to which 6 ml of deionized water is added to each flask to fully dissolve the polymers with stirring. To the dissolved polymers 5, 10, 15, 20, and 25 molar excess of EDC and N-boc ethylenediamine (0.165, 0.33, 0.495, 0.66 and 0.825 mmoles respectively) are then added to each of the respective reaction mixtures, which is stirred in an oil bath at 40° C. in the dark under a nitrogen atmosphere for 4 hrs (FIG. 1, Intermediate 2). After this time, the reaction solutions are transferred to separate dialysis bags (MWCO 2000) and dialyzed against deionized water for 2 days to purify the copolymers from the starting materials. The dialyzed polymers are then transferred to sterile conical tubes and dried on a lyophilizer for 2 days. The resulting polymers are characterized with $^1$H NMR, GPC, and MALDI-TOF.

Deprotection of N-boc-ethylenediamine Conjugated Reducible LLC

The acid-labile N-boc amine protection group present on the terminal end of the conjugated ethylenediamine is removed with TFA/$H_2O$ mixture (75/25 v/v). Briefly, 100 mg (0.033 mmoles) of reducible LLC is added to a round bottom flask to which 10 mL of deionized $H_2O$ is added. Afterwards, 30 ml of TFA is added. The dissolved copolymers are then stirred for 30 min at room temperature (FIG. 1, final product). The final polymers are then purified by dialysis (MWCO 2000) against deionized water for 2 days to remove the free N-boc groups and TFA. The dialyzed polymers are then transferred to a sterile conical tube and dried on a lyophilizer for 2 days. The resulting polymers are characterized with $^1$H NMR, GPC, and MALDI-TOF. The amount of primary amines in intermediate 1, intermediate 2, and the final product is quantified with a ninhydrin assay at 570 nm. The assay is conducted at 100° C. for 15 min. Glycine is used to construct the standard curves.

Chemical Structure Determination

LLC copolymers are synthesized through Michael addition using EDC as the coupling agent and the chemical structures are determined with $^1$H NMR (FIG. 1) (25). After synthesis and purification, chemical structure is determined with $^1$H NMR. The $^1$H NMR spectrum (300 MHz, $D_2O$) of intermediate 1 showed the following peaks: δ 1.231 (—NH—CH—$CH_2$—$CH_2$—$CH_2$—$CH_2$—NH—), δ 1.434 (—NH—CH—$CH_2$—$CH_2$—$CH_2$—$CH_2$—NH—), δ 1.581 (—NH—CH—$CH_2$—$CH_2$—$CH_2$—$CH_2$—NH—), δ 2.957 (—NH—CH—$CH_2$—$CH_2$—$CH_2$—$CH_2$—NH—), δ 3.178 (—NH—CH—$CH_2$—$CH_2$—$CH_2$—$CH_2$—NH—), δ 2.776 (—S—$CH_2$—$CH_2$—NH—), δ 3.436 (—S—$CH_2$—$CH_2$—NH—), δ 2.479 (—NH—$CH_2$—$CH_2$—CO—), δ 2.379 (—NH—$CH_2$—$CH_2$—CO—).

The $^1$H NMR spectrum (300 MHz, $D_2O$) of intermediate 2 showed the following peaks: δ 1.114 (—NH—CH—$CH_2$—$CH_2$—$CH_2$—$CH_2$—NH—), δ 1.518 (—NH—CH—$CH_2$—$CH_2$—$CH_2$—$CH_2$—NH—), δ1.719 (—NH—CH—$CH_2$—$CH_2$—$CH_2$—$CH_2$—NH—), δ 2.957 (—NH—CH—$CH_2$—$CH_2$—$CH_2$—$CH_2$—NH—, —S—$CH_2$—$CH_2$—NH—), δ 3.183 (—NH—CH—$CH_2$—$CH_2$—$CH_2$—$CH_2$—NH—, —NH—CH$_2$—CH$_2$—NH—), δ 2.508 (—NH—CH$_2$—CH$_2$—CO—), δ 3.431 (—S—CH$_2$—CH$_2$—NH—), δ 1.331 (terminal N-boc group).

Figure 2:
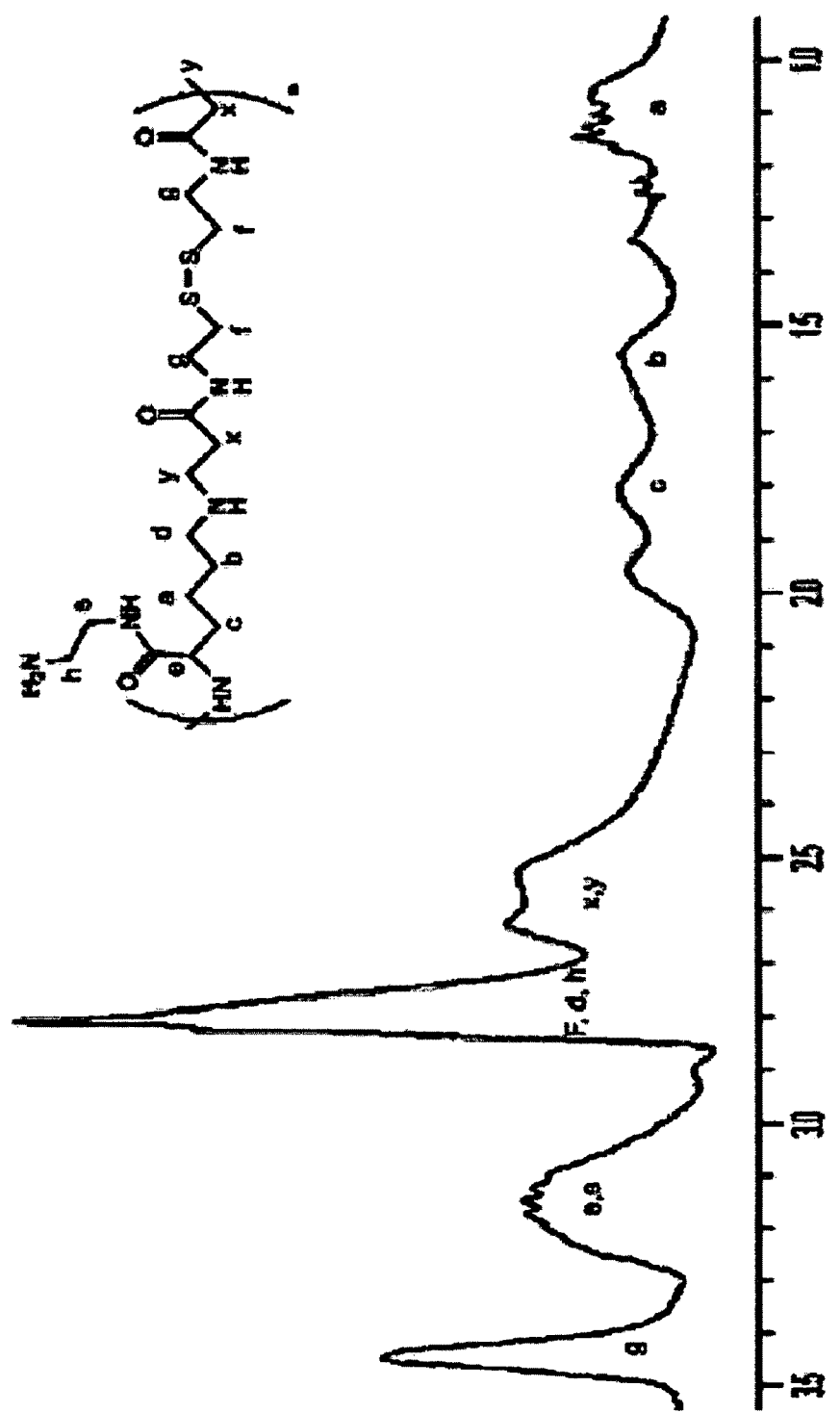
FIG. 2 is the $^1$H NMR spectra of final bioreducible lysine copolymer (LLC).

Finally, the $^1$H NMR spectrum (300 MHz, D$_2$O) of the final product showed the following peaks: δ 1.103 (—NH—CH—CH$_2$—CH$_2$—CH$_2$—CH$_2$—NH—), δ 1.565 (—NH—CH—CH$_2$—CH$_2$—CH$_2$—CH$_2$—NH—), δ 1.814 (—NH—CH—CH$_2$—CH$_2$—CH$_2$—CH$_2$—NH—), δ 2.811 (—NH—CH—CH$_2$—CH$_2$—CH$_2$—CH$_2$—NH—, —S—CH$_2$—CH$_2$—NH—, —NH—CH$_2$—CH$_2$—NH$_2$), δ 3.178 (—NH—CH—CH$_2$—CH$_2$—CH$_2$—CH$_2$—NH—, —NH—CH$_2$—CH$_2$—NH$_2$), δ 2.562 (—NH—CH$_2$—CH$_2$—C—), δ 3.456 (—S—CH$_2$—CH$_2$—NH—) (FIG. 2). The number of conjugated ethylenediamine per polymer chain for the final polymer using 5, 10, 15, 20 and 25 excess molar ratio of EDC and N-boc-ethylenediamine is 1.95, 3.33, 3.84, 7.51 and 2.3 respectively (Table 1). The reducible LLC copolymers with 20 excess molar ratio of EDC and N-boc-ethylenediamine showed the maximum amount of ethylenediamine conjugation as determined with $^1$H NMR and it is then designated the optimum reducible LLC and selected for use in subsequent assays.

Figure 3:
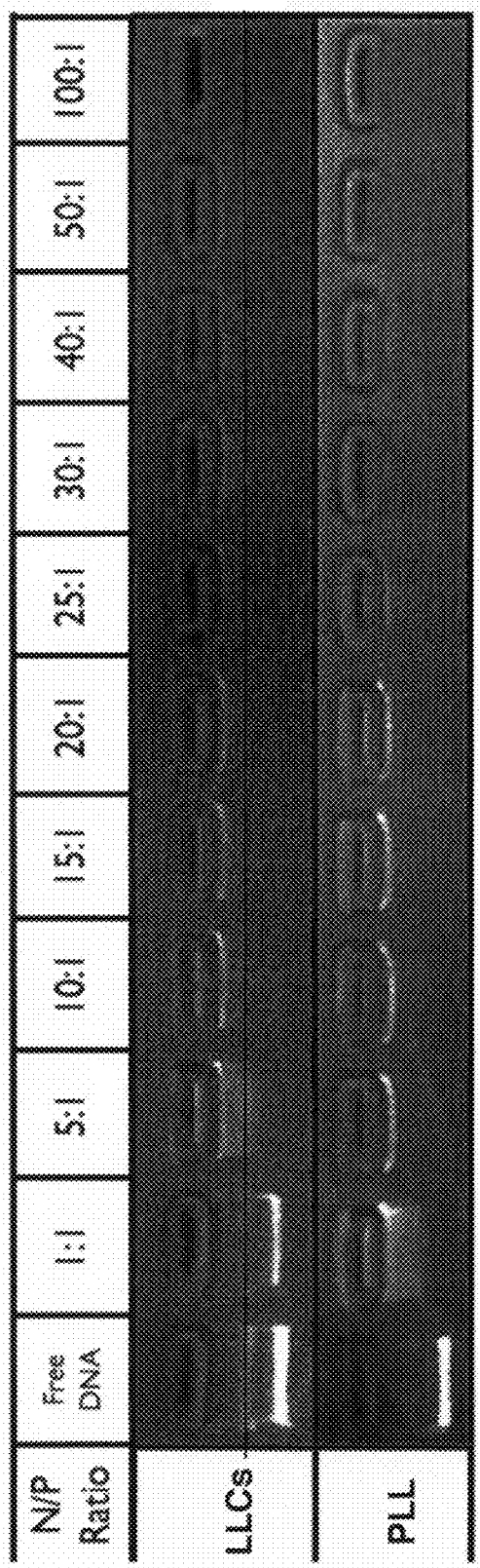
FIG. 3 shows an agarose gel electrophoresis of LLCs and PLL with plasmid DNA polyplexes as a function of N/P ratio (Lane 1, naked pDNA; lanes 2-11, LLC/pDNA and PLL/pDNA at N/P ratios of 1:1, 5:1, 10:1, 15:1, 20:1, 25:1, 30:1, 40:1. 50:1 and 100:1).

The degree of EDA conjugation to the copolymer backbone as determined with $^1$H NMR, was found to be 25, 42, 48, 94 and 29% for the 5, 10, 15, 20, and 25 molar excess of N-boc EDA respectively. Thus, the data showed that only a maximum of 94% conjugation of EDA to the polymer chains was possible, which was probably due to steric hindrance of approaching nearby EDA molecules at higher molar concentrations that limit further conjugation to the polymers. The reducible LLCs with 94% conjugated EDA was then used in subsequent assays as the final LLCs. PLL was able to effectively condense pDNA from an N/P ratio of 1/1 as evident by the absence of free pDNA from wells of the gel (FIG. 3, lanes 2-11) compared to LLCs where effective condensation occurred from an N/P ratio of 5/1 (FIG. 3, lanes 3-11). This could be due to the high MW PLL (~20900 Da) chains that would be more effective at condensing pDNA at this N/P ratio compared to low the MW LLC (~3200 Da) chains. However, both reducible LLCs and PLL were able to completely condense pDNA from an N/P ratio of 25/1 as apparent from the total absence of fluorescence in the wells (FIG. 3, lanes 7-11).

TABLE 1

| Final copolymers synthesized with excess molar ratios of EDC and N-boc-ethylenediamine | Actual % conjugation of ethylenediamine per repeating block | Number of conjugated branches per polymer chain | Mn (KDa) | Mw (KDa) | PDI |
| --- | --- | --- | --- | --- | --- |
| 5  | 24.4% | 1.95 | 3.565 | 3.851 | 1.08 |
| 10 | 41.6% | 3.33 | 3.600 | 4.054 | 1.12 |
| 15 | 48%   | 3.84 | 3.540 | 3.698 | 1.04 |
| 20 | 93.9% | 7.51 | 3.601 | 3.831 | 1.06 |
| 25 | 28.8% | 2.3  | 3.423 | 3.701 | 1.08 |

Molecular Weight Determination

The molecular weight of the synthesized LLC copolymers is determined using SEC and MALDI-TOF. The number average molecular weight (Mn) of intermediate 1, intermediate 2 and final product as determined by SEC are 3489, 3118, and 3601 Da with a polydispersity index (PDI) of 1.08, 1.10 and 1.06 respectively (Table 2). The number average molecular weight (Mn) of the LLC copolymers as determined by MALDI-TOF supported the calculated SEC data with molecular weights of 3538, 3118 and 3468 Da for intermediate 1, intermediate 2 and the final product respectively. The PDI of each is found to be 1.097, 1.10 and 1.09 respectively (Table 2). For the final product this corresponds to 6-8 repeating units (MW=436.64 Da for each repeating unit). The ninhydrin assay confirmed that the final polymer had more primary amines ($1.44 \times 10^{-4} \pm 3.5 \times 10^{-5}$) compared to intermediate 1 ($1.27 \times 10^{-4} \pm 3.5 \times 10^{-5}$) and intermediate 2 ($1.03 \times 10^{-4} \pm 3.2 \times 10^{-5}$).

TABLE 2

| Polymers | Mn (KDa) | | Mn (KDa) | | PDI | | |
| --- | --- | --- | --- | --- | --- | --- | --- |
|  | SEC | MALDI-TOF | SEC | MALDI-TOF | SEC | MALDI-TOF | |
| Intermed. 1 | 3.489 | 3.538 | 3.771 | 3.881 | 1.08 | 1.097 | ~6-8 |
| Intermed. 2 | 3.118 | 3.118 | 3.443 | 3.429 | 1.10 | 1.10 | |
| Final Product | 3.601 | 3.468 | 3.831 | 3.780 | 1.06 | 1.09 | |

EXAMPLE 3

Reducible LLC/pDNA Polyplexes

Preparation

All polymer/pDNA complexes are freshly prepared prior to use. LLC/pDNA polyplexes are prepared through diluting 1.74 mg/mL aqueous solution of plasmid DNA (pCMV-Luc) to a desired concentration (10 μg/mL). Both polymer and plasmid are then diluted to the appropriate concentration depending on the required N/P ratio (nitrogens of polymer/phosphate of pDNA) each to a final volume of 200 μL containing 5% glucose. The pDNA solutions are then added to the polymer solutions in equal volumes and complexation is allowed for 30 min prior to use.

Particle Size and Zeta-Potential (ζ)

The particle size distribution of the LLC/pDNA polyplexes formed from the LLC copolymer with pCMV-Luc is determined by dynamic light scattering. The average particle size of LLC/pDNA polyplexes of N/P ratios 1/1, 5/1, 10/1, 15/1, 20/1 and 25/1 are found to be 231.9±22.6, 180.6±13.3, 158.3±12.9, 150.6±21.3, 151.6±12.5, 141.7±11.5, 143.9±10.1, 130.3±11.6 and 100.3±24.4 nm respectively (FIG. 4). Similarly, the PLL/pDNA polyplexes of N/P ratios 1/1, 5/1, 10/1, 15/1, 20/1 and 25/1, had average particle sizes of 258.7±41.0, 182.2±15.5, 176.6±23.2, 148.2±19.3, 121.3±14.6, 125.9±11.5, 112.9±8.1, 117.6±7.3 and 112.7±38.1 nm respectively (FIG. 4). Moreover, the particle size distribution of the polyplexes prepared from the LLC with pCMV-luc is found to be homogenous and unimodal as represented in the LLC polyplexes of N/P ratio of 25/1 (FIG. 4B). The zeta potential of LLC/pDNA polyplexes of N/P ratios 1/1, 5/1, 10/1, 15/1, 20/1 and 25/1 are −4.1±4.4, −1.0±2.8, 0.9±2.0, 5.8±2.5, 5.0±1.2, 8.4±2.1, 8.3±2.5, 15.0±2.7, 16.6±2.8 mV respectively (FIGS. 5A-5B). Similarly, the zeta potential of the control PLL/pDNA polyplexes of N/P ratios 1/1, 5/1, 10/1, 15/1, 20/1 and 25/1 are −3.0±2.2, 2.1±2.6, 0.5±4.7, 4.9±2.0, 5.9±2.3, 6.9±1.0, 13.0±2.0, 10.2±3.4, 14.0±4.4 mV respectively with excellent fit to the theoretical polynomial values (FIG. 4B).

Figure 4A:
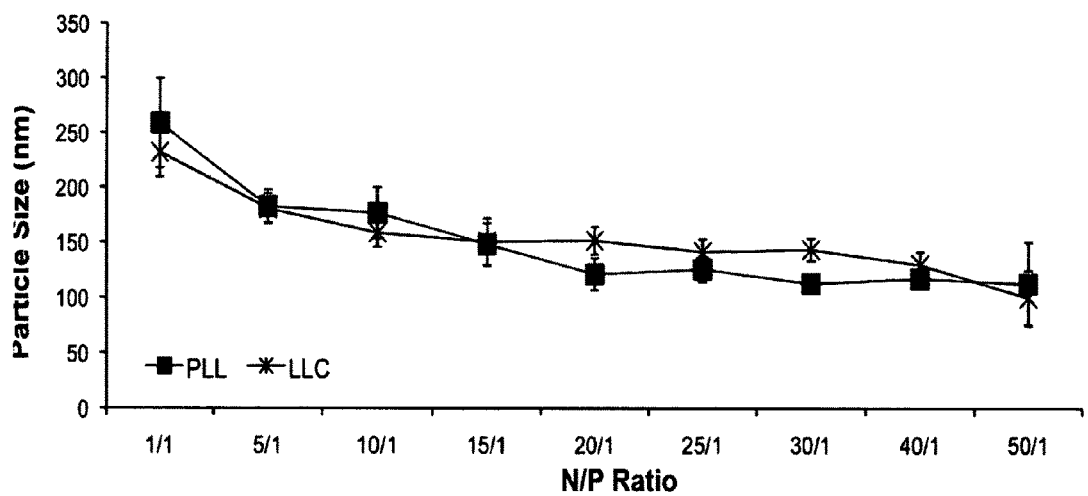
FIGS. 4A-4B are a particle size analysis of various LLC/pDNA polyplexes using dynamic light scattering as a function of N/P ratio. Average particle sizes of LLC/pDNA and PLL/pDNA polyplexes were measured at different N/P ratios from 1:1 to 50:1 (FIG. 4A). A representative particle size distribution of the polyplexes prepared from the LLCs with pCMV-luc plasmids at N/P ratio of 25/1 is shown (FIG. 4B). Data represented as mean±SD, N=3.
Figure 4B:
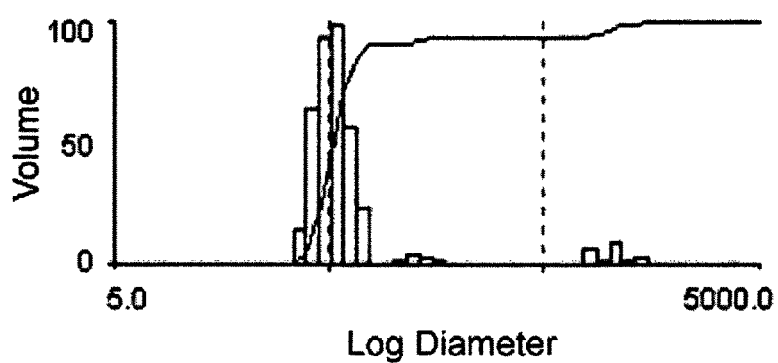
Figure 5A:
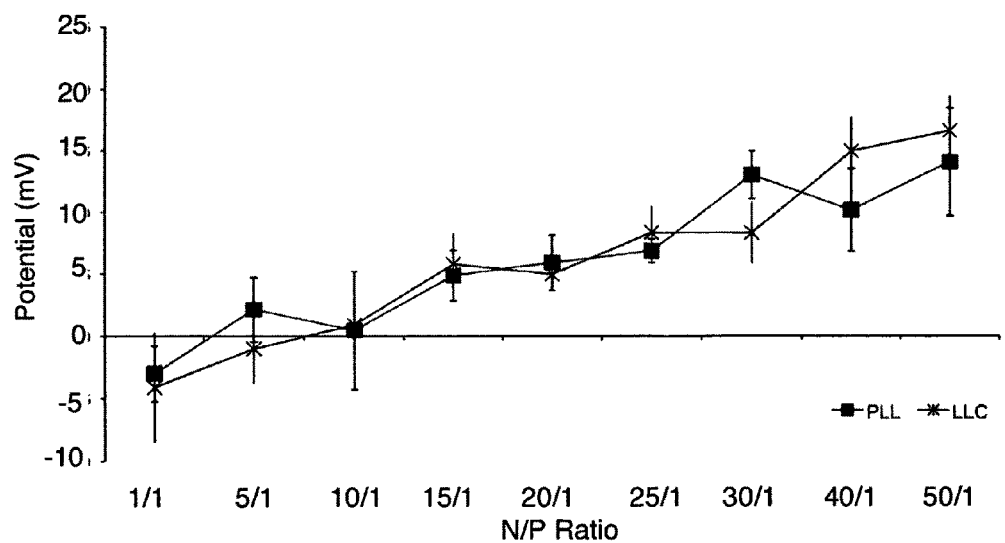
FIGS. 5A-5B show the Zeta potential ($\zeta$) of LLC/pCMV-Luc polyplexes as a function of N/P ratio (FIG. 5A). A representative zeta potential profile of the polyplexes prepared from the LLCs with pCMV-luc plasmids at N/P ratio of 25/1 is shown (FIG. 5B). Data represented as mean±SD, N=3.
Figure 5B:
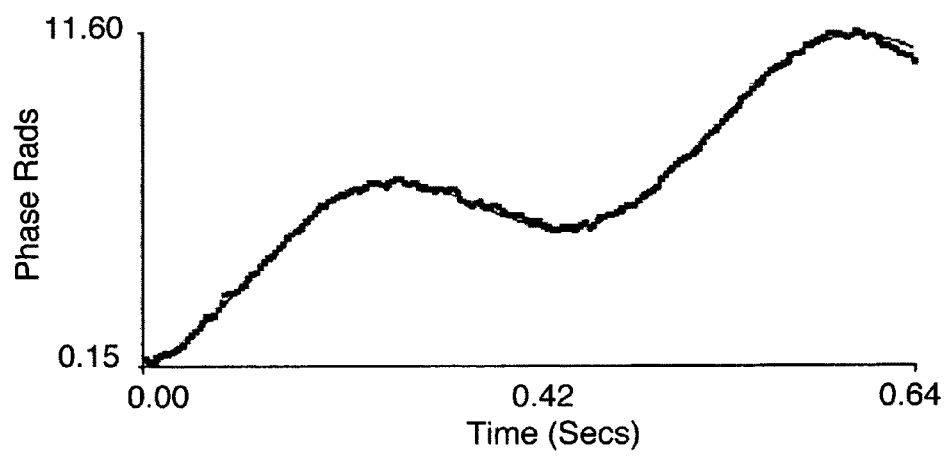

The particle size distribution of the LLC/pDNA polyplexes showed that N/P ratios greater than 5/1 can efficiently condense pDNA into nanoparticles with effective diameters of less than 150 nm (FIGS. 4A-4B). In addition, the LLC copolymers produced slightly larger polyplexes than PLL, which could be attributed to the lower molecular weight chains as compared to the high molecular weight PLL chains. Overall, the majority of the polyplexes remained constant at ~150 nm at various N/P ratios in comparison to PLL, which showed an average particle size of ~125 nm from an N/P ratio of 20/1. Moreover, the particle size distribution of the LLC/pDNA polyplexes was found to be homogenous (FIG. 4B), which could reflect the narrow PDI of the synthesized polymer chains. The zeta potential of the LLC/pDNA polyplexes ranged from ~−4±4.4 mV for N/P ratio of 1/1 to a maximum surface charge of ~17±2.85 mV for N/P ratio of 50/1 (FIGS. 5A-5B) and the zeta potential of the PLL/pDNA polyplexes ranged from ~−3±2.21 for N/P ratio of 1/1 to a maximum surface charge of ~14±4.3 mV for N/P ratio of 50/1 (FIGS. 5A-5B). There were no significant differences in zeta potential values between PLL and LLCs, which indicated the accuracy of the formulation of the polyplexes based on N/P ratios ($p$-value$>0.05$). Furthermore, the calculated zeta potential values of the LLC polyplexes were found to fit the extrapolated polynomial equation (FIG. 5B), which reflected the accuracy of the zeta potential measurements for both LLCs and PLL polyplexes using Smoluchowski's equation.

EXAMPLE 3

Transfection and Cytotoxicity of Polyplexes

In Vitro Transfection Efficiency

Figure 6A:
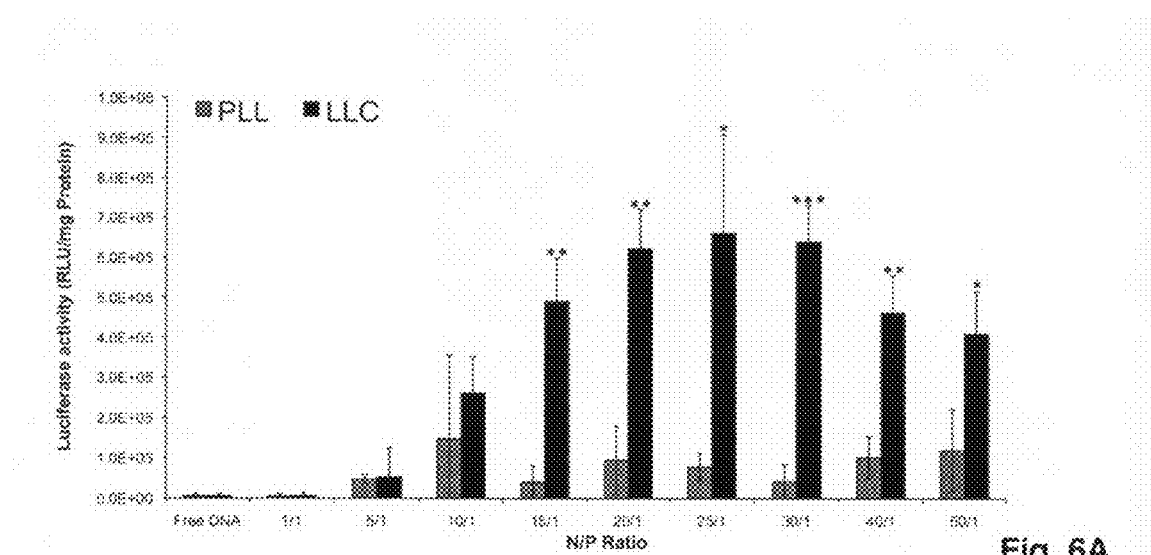
FIGS. 6A-6C show the In-vitro transfection efficiency of the polyplexes of pCMV-Luc with LLC polymer in HDFs (FIG. 6A), MCF-7s (FIG. 6B) and 4T1s (FIG. 6C) cells in comparison with same N/P ratio PLL. Data are averages of three parallel experiments.
Figure 6B:
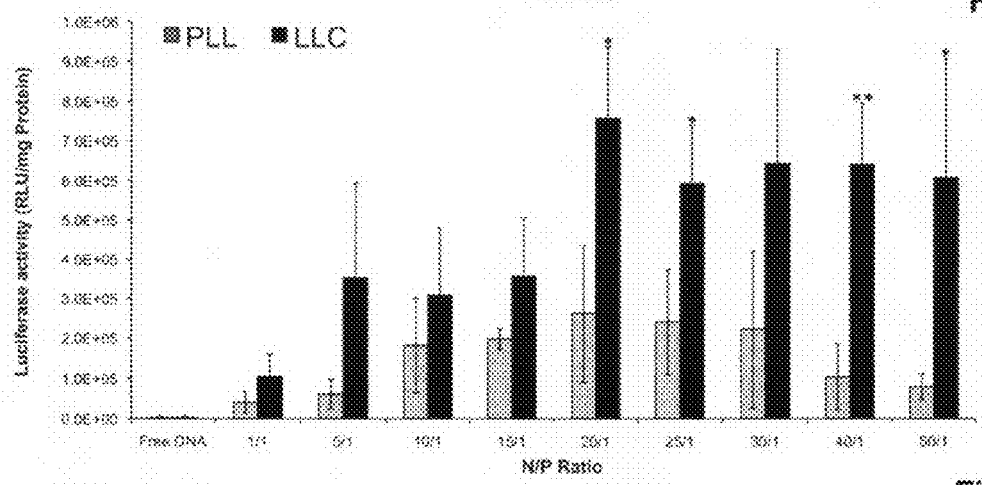
Figure 6C:
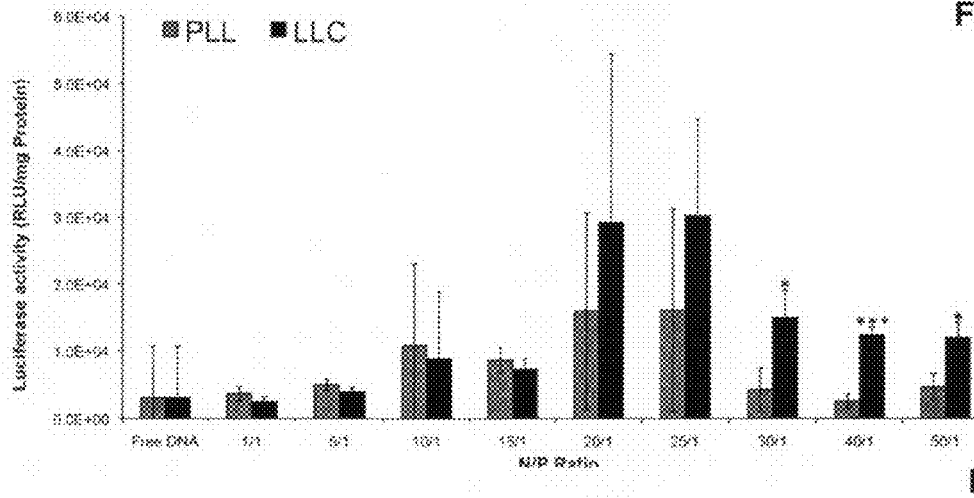
Figures 8A, 8B, 8C:
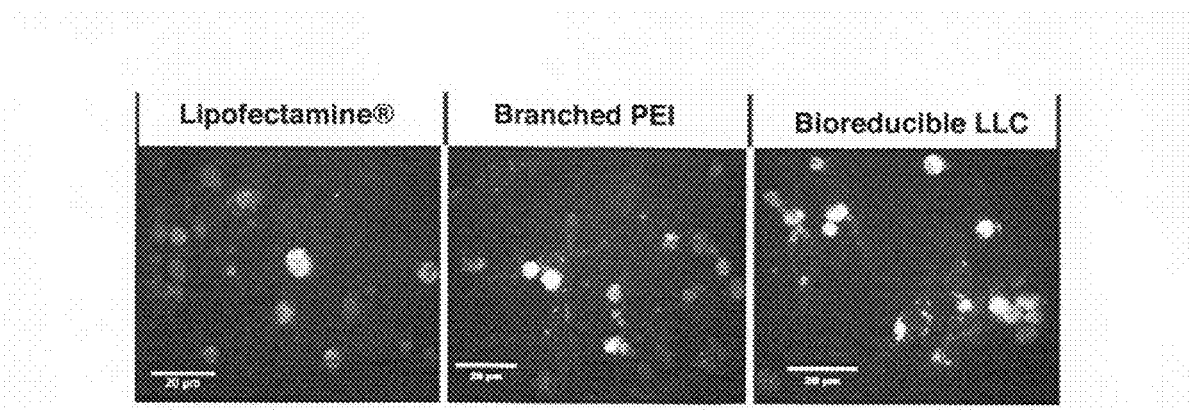
FIGS. 8A-8D are fluorescence microscopy images of transfected HDF cells with pCMV-EGFP complexed with either branched PEI (FIG. 8A), Lipofectamine® (FIG. 8B) and reducible LLCs (FIG. 8C) at N/P ratio of 25/1 after 48 hr of transfection.

The luciferase assay showed that LLC/pDNA polyplexes of N/P ratio 40/1 resulted in a 5.5-fold higher transfection efficiency in comparison to the optimal PLL control at an N/P ratio of 50/1 in HDF cells ($p<0.05$) (FIG. 6A). The LLC/pDNA polyplexes of N/P ratio 20/1 showed a 3-fold higher gene transfection efficiency than the optimal PLL control at an N/P ratio of 20/1 in MCF-7 cells ($p<0.05$) (FIG. 6B). In MA cells, the LLC/pDNA polyplexes at an N/P ratio of 50/1 resulted in a 4.4-fold higher gene transfection efficiency than the optimal PLL control at an N/P ratio of 50/1 ($p<0.05$) (FIG. 6C). These higher transfection efficiencies of the LLCs as compared to the PLL control could be attributed to the more efficient release of the pDNA from the LLC polyplexes into the cytosol of the cells as a result of reduction of the disulfide bonds along the polymer backbone. In addition, the higher transfection efficiencies of the LLCs could also be due to the higher cell viabilities of the cells treated with the LLC polyplexes as compared with the PLL control (FIG. 8A-8C, discussed below). The LLC/pDNA polyplexes at an N/P ratio of 25/1 was selected as the optimum complexes for use in subsequent studies since these produced high transfection efficiencies in both HDF and MCF-7 cells with the least cytotoxicity in all cell lines.

Figure 7:
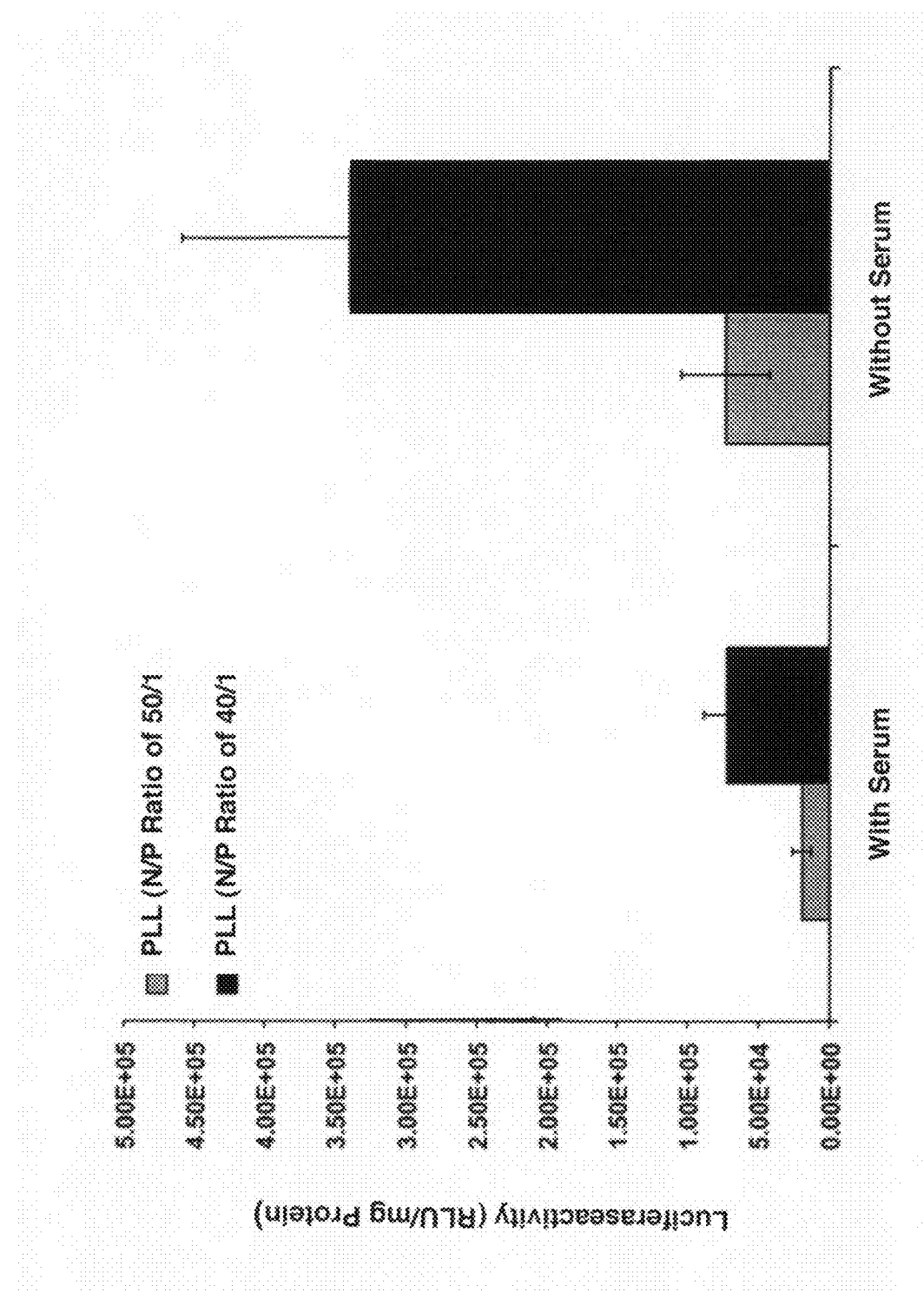
FIG. 7 shows the in vitro transfection efficiency of the LLC/pCMV-Luc polyplexes in serum at optimal N/P ratio for PLL (N/P of 50/1) and LLCs (N/P of 40/1) in HDF cells. Data represented as mean±SD, N=3.

The effect of serum on the transfection efficiency of LLC polyplexes was investigated at the N/P ratios for LLC and PLL polyplexes that produced the highest transfection efficiencies (50/1 and 40/1 respectively) in HDF cells (FIG. 7. The results showed that LLCs and PLL polyplexes in serum produced a 5-fold and 4-fold reduction in luciferase activity respectively. This could be due to the binding of the positively charged polyplexes with the negatively charged serum proteins that typically reduce the cellular uptake of polymer/pDNA polyplexes (37). However, the relative difference in transfection efficiency between LLCs and PLL polyplexes was found to be serum independent, since the statistical significance was maintained despite the presence of serum ($p$-value$<0.05$).

Figure 8D:
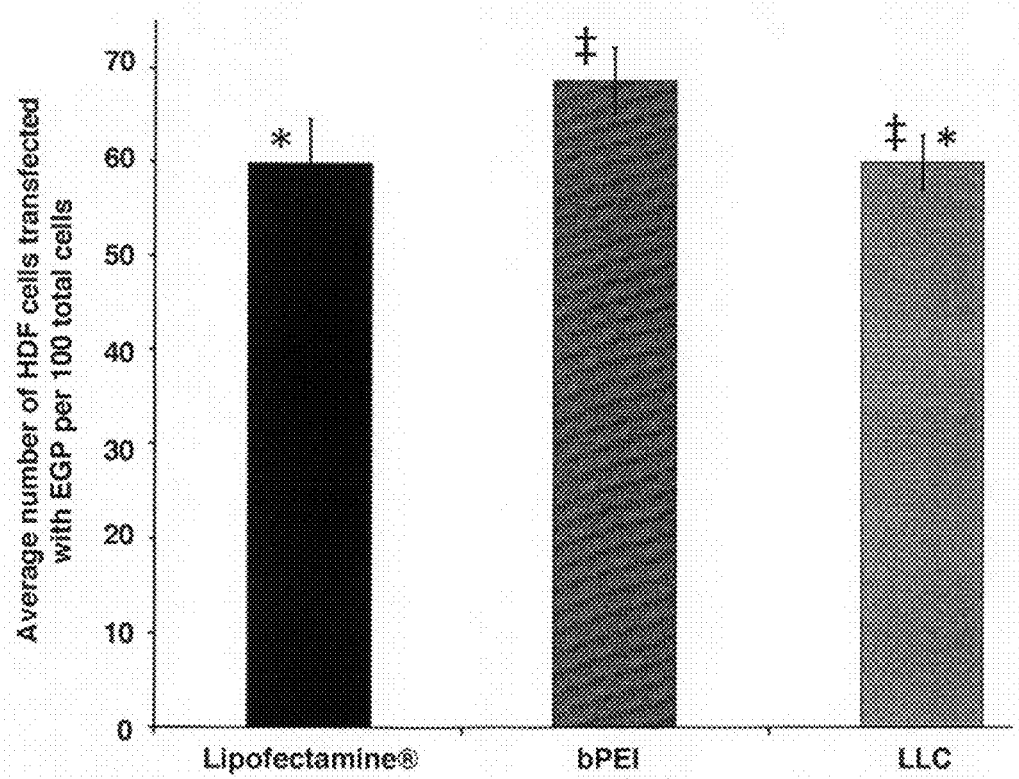

To compare the transfection efficiency of the LLC polyplexes with commercial nonviral vectors, HDF cells were also transfected with PEI and Lipofectamine® complexed with pCMV-EGFP plasmids. The fluorescence microscopy data (FIG. 8A-8C) showed that the transfection efficiency of the bioreducible LLC polyplexes was comparable to the commercial vectors. Specifically, quantitative analysis of the data showed that the percentage of cells expressing EGFP from the LLC/pDNA polyplexes was not significantly different from the gene expression obtained from the PEI and Lipofectamine® commercial vectors ($p>0.05$) (FIG. 8D). These data confirmed that LLCs are efficient gene transfection agents compared to commercially used nonviral transfection agents such as PEI and Lipofectamine®.

Cytotoxicity of LLC Copolymers

Figure 9A:
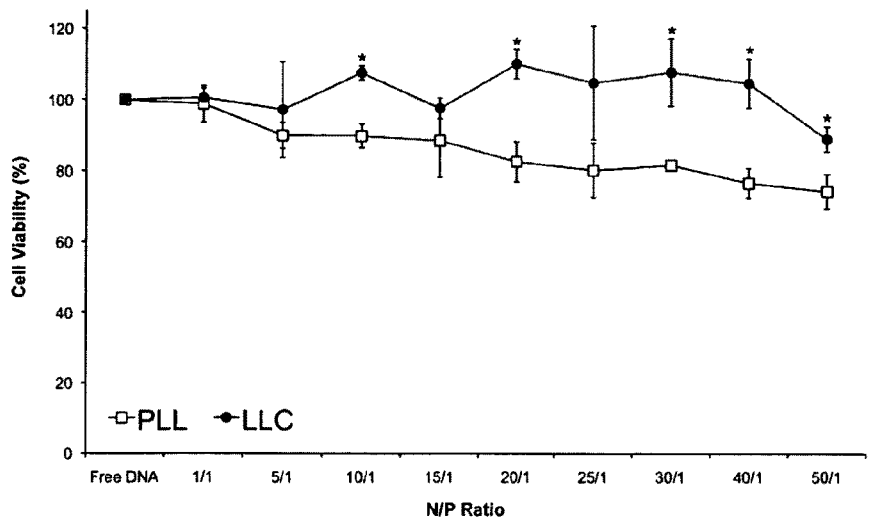
FIGS. 9A-9C show cell viability of LLC/pCMV-Luc polyplexes as a function of N/P ratios with an MTT assay for (FIG. 9A) HDF cells, (FIG. 9B) MCF-7 cells, and (FIG. 9C) MA cells. Data represented as mean±SD, N=3. (* indicates p-value<0.05).
Figure 9B:
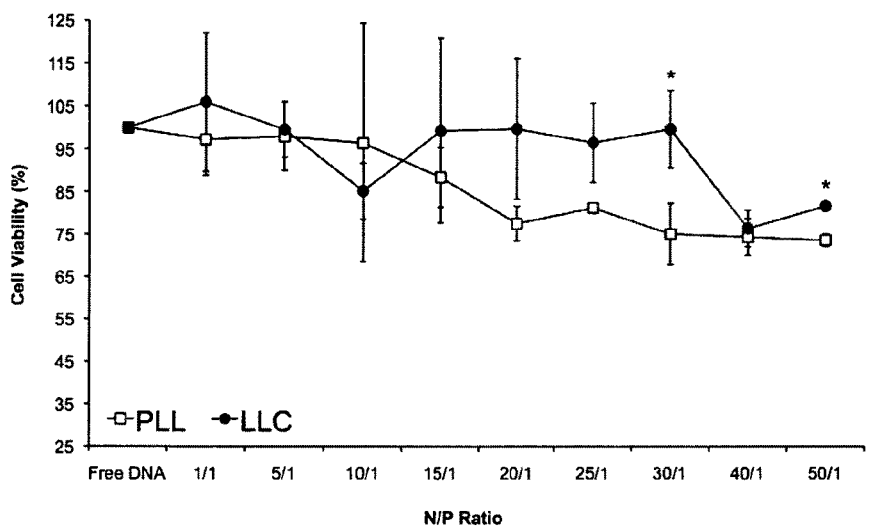
Figure 9C:
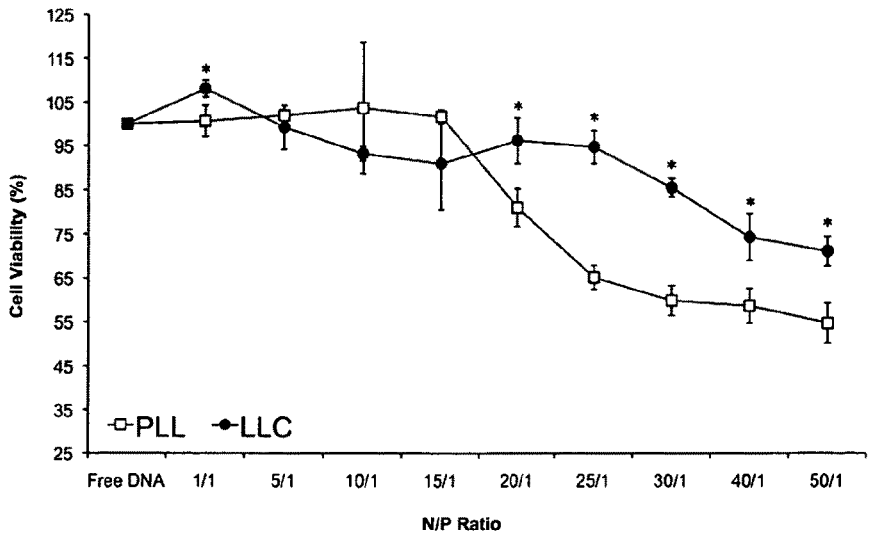

The MTT assay showed that LLC polyplexes produced lower cytotoxicity compared to PLL at N/P ratios up to 50/1. LLC polyplexes at 20/1 N/P ratio maintained the highest cell viability in all three cell lines in comparison to PLL at the same N/P ratio. PLL at 20/1 N/P ratio showed a decrease in cell viability to 82%, 77% and 81% for HDF, MCF-7 and MA cells respectively with ~100% cell viability for LLC/pDNA polyplexes in the three cell lines (FIG. 9A-9C). PLL at 25/1 N/P ratio resulted in a decrease in cell viability to 80%, 81% and 65% for HDF, MCF-7 and MA cells respectively as compared to ~100% cell viability for LLC/pDNA polyplexes in the three cell lines at this N/P ratio (FIG. 9A-9C). In addition, LLC polyplexes produced almost no cytotoxicity in HDF cells at N/P ratios from 1/1 to 40/1 compared to PLL ($p<0.05$). For an N/P ratio of 30/1, LLC polyplexes showed ~100% cell viability for the three cell lines as compared to PLL at the same N/P ratio, which produced an 81%, 75% and 60% reduction in cell viability in for HDF, MCF-7 and MA cells respectively.

Moreover, a cell viability of ~100% was maintained for LLC/pDNA polyplexes as compared to a reduced 75% cell viability for PLL from an N/P ratio of 1/1 to 30/1 for MCF-7 cells ($p<0.05$). Finally, LLC/pDNA polyplexes showed negligible cytotoxicity in MA cells at N/P ratios from 1/1 to 25/1 compared to PLL ($p<0.05$). However, the cytotoxicity of LLC/pDNA polyplexes in MA and MCF-7 cells was higher than that of HDF cells at N/P ratios of 40/1 and 50/1. This observation influenced our choice of the HDF cell line for use in previous studies. These improvements in cell viability for LLCs as compared to PLL could be due to the low molecular weight LLC copolymers and their byproducts, which produce lower charge densities and hence lower cytotoxicities as compared to high molecular weight PLL. The cytotoxicities of high molecular weigh PLL has been extensively studied in various cells lines, which have shown that high charge densities can result in an increase in cellular toxicities (30, 38-42).

Confocal Microscopy Study of HDF Cells Transfected with EMA Labeled pDNA

The confocal microscopy data showed red punctate staining indicative of the presence of EMA-labeled pDNA in the cytosol, aggregated around the nucleus, and possibly within the nucleus of DAPI-stained cells transfected with LLC/pDNA polyplexes after 4, 8, and 12 hrs (FIGS. 10A-10C). The delivery of the pDNA in and around the nucleus could reflect the efficient reduction of the disulfide bonds of the copolymer chains and hence efficient release of pDNA that was trafficked to the nucleus. However, since the polymers were not labeled, the observed fluorescence could have represented either free pDNA or pDNA still associated with the copolymers after disulfide reduction, which was actually shown in the DTT fluorescence assay (see discussion for FIGS. 12A-12B). These data together with the fluorescence microscopy studies (FIGS. 8A-8D) suggested that low MW reducible LLCs were capable of delivering its DNA cargo into the cytosol and possibly into the nucleus of transfected cells, which resulted in transfection efficiencies comparable to higher MW non-degradable systems without compromising cell viabilities, which is a known limiting factor for commercial delivery systems such as PEI (30-31, 43-44).

In-Vitro Reduction Studies

The mechanism of pDNA release from the LLC/pDNA polyplexes was investigated in two reduction assays with the optimized 25/1 N/P ratio polyplexes. In the first study, a gel retardation assay was used to verify pDNA release from the polyplexes as a function of DTT concentration. This data showed that the reduction of the disulfide bonds occurred from a low concentration of ~0.5 mM, which was apparent from the increase in fluorescence in the wells but that higher concentrations of ≥3 mM DTT were required to completely reduce the disulfide bonds so as to release the pDNA from the polyplexes (FIG. 11A, lanes 10-12). Since the intracellular concentration of the reducing agent glutathione (GSH) has been found to be 1-11 mM depending on the cell type, the reduction of LLC/pDNA polyplexes at 3 mM DTT showed that there would be an adequate concentration of GSH in cells to completely reduce the synthetic disulfide bonds of the LLCs (45). However, even though ≥90% of the pDNA was released from the polyplexes upon reduction, residual pDNA was observed in the wells of the gel retardation assay (FIG. 11B, lanes 12) despite treatment with ≥40 mM DTT (data not shown).

Figure 12B:
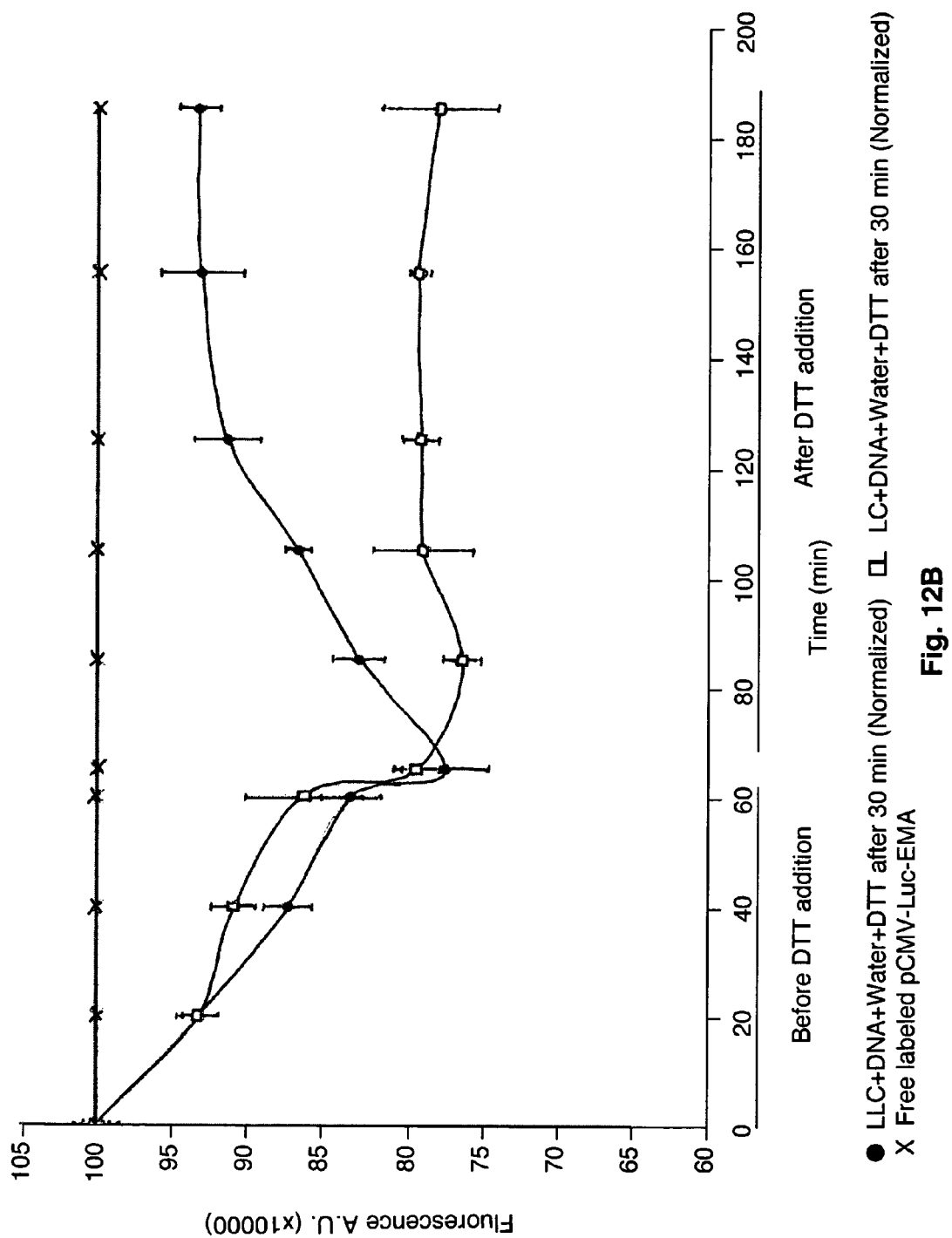

Thus, to investigate whether or not all of the plasmids were released after treatment with DTT in solution, pDNA was fluorescently labeled with EMA and treated the LLC polyplexes with 4 mM DTT in a second reductive assay. As shown in FIGS. 11A-11B, the fluorescence of the labeled pDNA diminished rapidly after the addition of the LLCs, which corresponded to pDNA complexation (FIG. 12A, lanes 3 and 4). The subsequent addition of DTT resulted in an increase in fluorescence as opposed to the non-reducible PLL control but only to ~90% of the original fluorescence (FIG. 12B). These data indicated that some of the pDNA remained associated with the LLCs despite complete reduction of the disulfide bonds, which could be due to the residual electrostatic interactions between the positively charged polymer fragments and the negatively charged pDNA. These findings were thus consistent with the gel retardation assay.

DNase Protection Assay

Figure 13:
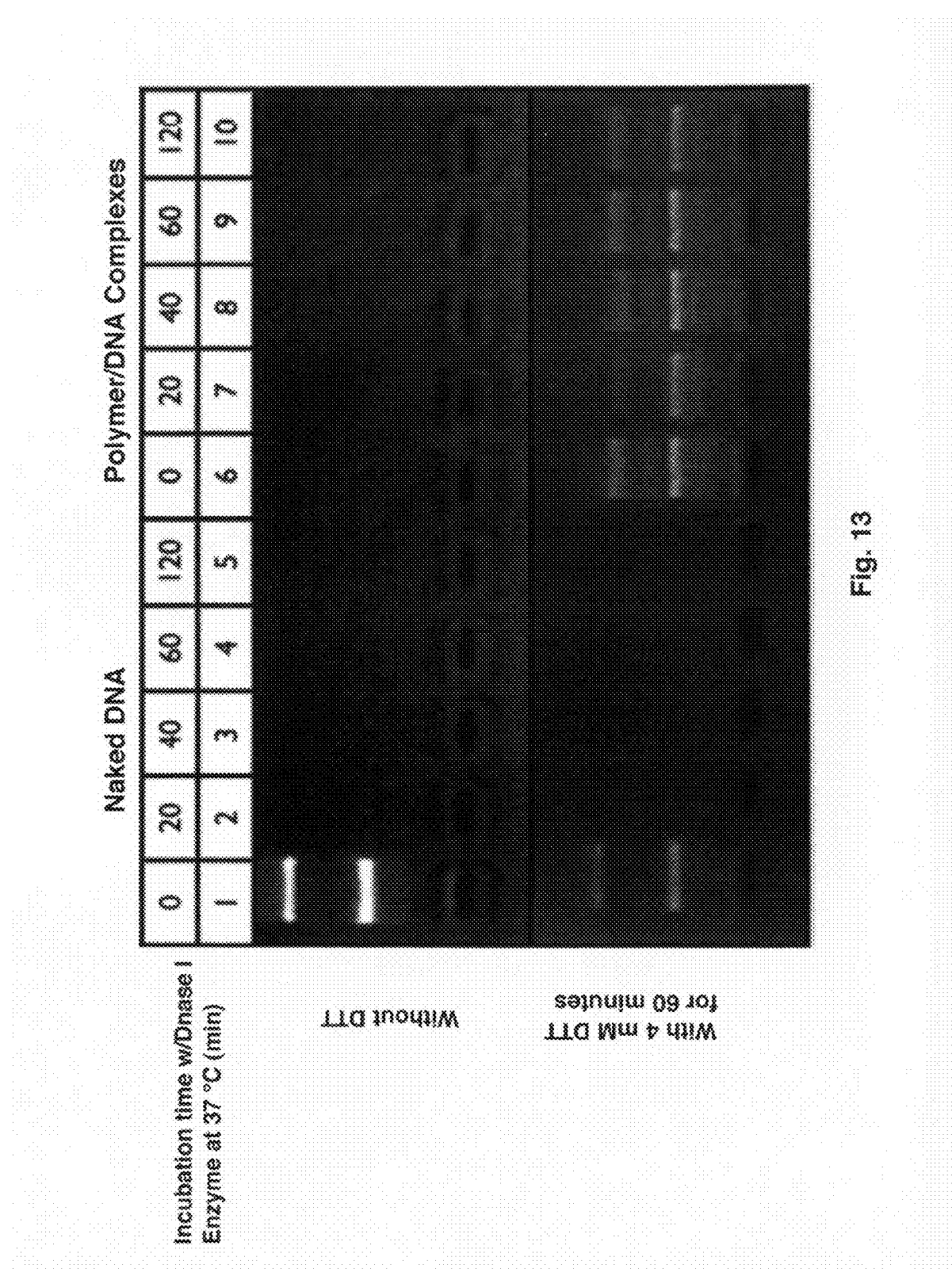
FIG. 13 shows the DNase I protection assay for LLC/pDNA polyplexes at 25/1 N/P ratio. Lanes 1-5 and 6-10 represent dissociated and reisolated plasmids from naked pDNA and polymer/pDNA polyplexes respectively after exposure to DNase I (1) without DTT and (2) with 4 mM DTT for 120 min followed by electrophoresis on a 1% agarose gel at 80 V for 60 min

The DNase I protection assay showed that the LLCs were able to form tight polyplexes, which completely protected the pDNA from degradation by the endonucleases for up to 2 hr (FIG. 13, lane 10). In contrast, the naked pDNA was fully degraded by DNase I in 20 min, as shown in FIG. 11, lane 2, and in 40 min, all the naked pDNA was completely degraded. This is opposed to the pDNA that was released from the polyplexes only after the addition of DTT for 60 min. LLC polyplexes protected the pDNA at all time points from endonuclease digestion as shown by the intact pDNA bands on the stained agarose gel (FIG. 13, lanes 6-10). The stability of these polyplexes in the non-reducing environment is very important to ensure safe delivery of the therapeutic plasmid to its target. Moreover, the data showed that pDNA release only occurred in a reductive environment, despite the presence of other negatively charged SDS molecules that typically exchange with the polycationic carriers to release the DNA cargo in this assay. The unusual stability of these reducible complexes could be due to the low molecular weight polymers that effectively coat the DNA macromolecules to produce very stable complexes.

The following references are cited herein.
1. Mansouri et al. Eur J Pharm Biopharm 57(1) 1-8 (2004).
2. Sano et al. Adv Drug Deliv Rev 55(12) 1651-1677 (2003).
3. Oupick et al. Bioconjug Chem 11(4) 492-501 (2000).
4. Eliyahu et al. Molecules 10(1) 34-64 (2005).
5. Vasir et al. Expert Opin Drug Deliv 3(3) 325-344 (2006).
6. Lungwitz et al. Eur J Pharm Biopharm 60(2) 247-266 (2005).
7. Satija et al. Crit Rev Ther Drug Carrier Syst 24(3) 257-306 (2007).
8. Ou et al. Bioconjug Chem 19(3) 626-633 (2008).
9. Hung et al. J Control Release 133(1):68-76 (2009).
10. Green et al. Nano Lett 8(10):3126-3130 (2008).
11. Arote et al. J Gene Med 10(11):1223-1235 (2008).
12. Yamanouchi et al. Biomaterials 29(22):3269-3277 (2008).
13. Xu et al. Am J Respir Crit Care Med 178(1):60-73 (2008).
14. Bikram et al. J Control Release 103(1):221-233 (2005).
15. Shim and Y. J. Kwon. Bioconjug Chem (2009).
16. Shim and Y. J. Kwon. J Control Release 133(3):206-213 (2009).
17. Shim and Y. J. Kwon. Biomacromolecules 9(2):444-455 (2008).
18. Jiang et al. Biomed Mater 3(2):25013 (2008).
19. Yang et al. Int J Pharm 353(1-2):277-282 (2008).
20. Jun et al. Bioorg Med Chem Lett 17(11) 2975-2978 (2007).
21. Luten et al. J Control Release 89(3) 483-497 (2003).
22. Saito et al. Adv Drug Deliv Rev 55(2) 199-215 (2003).
23. Hoon Jeong et al. Biomaterials 28(10) 1912-1917 (2007).
24. Peng et al. Bioconjug Chem 19(2) 499-506 (2008).
25. Breunig et al. J Control Release (2008).
26. Christensen et al. J Control Release 118(2):254-261 (2007).
27. Christensen et al. Bioconjug Chem 17(5):1233-1240 (2006).
28. Kim et al. Biomaterials 29(33):4439-4446 (2008).
29. Kim et al. Molecular Pharmaceutics 0(0) (December 2008, Web edition).

30. Hong et al. Bioconjug Chem 17(3):728-734 (2006).
31. El-Aneed. J Control Release 94(1):1-14 (2004).
32. Li et al. Biomacromolecules 10(8):2284-2293 (2009).
33. Walsh et al. Mol Pharm 3(6):644-653 (2006).
34. Yamagata et al. Bioorg Med Chem 15(1):526-532 (2007).
35. Jeon et al. J Biomed Mater Res A 66(4):854-859 (2003).
36. Suh et al. J Control Release 72(1-3):171-178 (2001).
37. Yang et al. Gene Ther 4(9):950-960 (1997).
38. Gonzalez et al. Bioconjug Chem 10(6):1068-1074 (1999).
39. Choi et al. Hum Gene Ther 10(16):2657-2665 (1999).
40. Toncheva et al. Biochim Biophys Acta 1380(3):354-368 (1998).
41. Choi, et al. Bioconjug Chem 9(6):708-718 (1998).
42. Choi et al. J Control Release 54(1):39-48 (1998).
43. Brunot et al. Biomaterials 28(4):632-640 (2007).
44. Godbey et al. Biomaterials 22(5):471-480 (2001).
45. Schafer et al. Free Radic Biol Med 30(11):1191-1212 (2001).

One skilled in the art will appreciate readily that the present invention is well adapted to carry out the objects and obtain the ends and advantages mentioned, as well as those objects, ends and advantages inherent herein. The present examples, along with the molecules, specific compounds, methods, procedures, treatments, etc. described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A biodegradable copolymer having the chemical structure of:

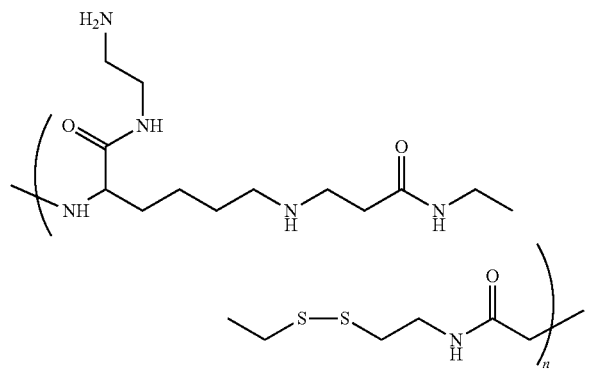

wherein n is 1 to about 10 repeating units.

2. The biodegradable copolymer of claim 1, further comprising a targeting moiety.

3. The biodegradable copolymer of claim 1, further comprising one or more moieties effective to facilitate endosomal escape.

4. The biodegradable copolymer of claim 1, wherein n is about 6 to about 10 repeating units.

5. A pharmaceutical composition comprising the biodegradable copolymer of claim 1 and a pharmaceutically acceptable carrier.

6. A nanoplex delivery system, comprising:
    the biodegradable copolymer of claim 1; and
    a cargo molecule complexed thereto.

7. The nanoplex delivery system of claim 6, wherein the cargo molecule is a nucleic acid, a polynucleotide or other biomolecule.

8. The nanoplex delivery system of claim 7, wherein the cargo molecule is DNA, plasmid DNA, a siRNA, an introgen or an antisense nucleotide.

9. The nanoplex delivery system of claim 6, wherein the nanoplex delivery system has a nitrogen:phosphate ratio of about 1:1 to about 50:1.

10. A method for treating a pathophysiological condition in an subject, comprising:
    delivering the cargo molecule comprising the nanoplex delivery system of claim 6 one or more times to a cell associated with the pathophysiological condition in the subject, wherein transfection of the cell with the cargo molecule elicits a therapeutic response, thereby treating the pathophysiological condition.

11. The method of claim 10, further comprising administering one or more times concurrently or consecutively one or more other therapeutic compounds or pharmaceutical compounds to the subject.

12. A method for increasing biocompatibility of a polymeric delivery system upon delivery to a subject, comprising:
    complexing the biodegradable copolymer of claim 1 with a biomolecule thereby forming a nanoplex; and
    delivering the nanoplex to the subject, whereupon reduction of the polymer backbone, the biomolecule is released from the nanoplex and the nanoplex degrades into biodegradable lysine subunits, thereby improving biocompatibility of the polymeric delivery system with the subject.

13. The method of claim 12, further comprising conjugating diethylamine along the copolymer backbone to sequester lysine hydroxyl groups.

14. The method of claim 12, further comprising conjugating one or both of a targeting moiety or one or more moieties effective to facilitate endosomal escape to the biodegradable copolymer.

15. The method of claim 12, wherein the biomolecule is a nucleic acid or polynucleotide.

16. The method of claim 15, wherein the biomolecule is DNA, plasmid DNA, siRNA, an nitrogen, or an antisense nucleotide.

17. A nanoplex delivery system, comprising:
    the biodegradable copolymer of claim 1; and
    a nucleic acid or polynucleotide complexed thereto.

18. The polymeric delivery system of claim 17, wherein the nucleic acid is plasmid DNA, a siRNA, an nitrogen or an antisense nucleotide.

19. The polymeric delivery system of claim 17, wherein the nanoplex delivery system has a nitrogen:phosphate ratio of about 1:1 to about 50:1.

* * * * *